United States Patent
Mase et al.

(10) Patent No.: US 9,024,224 B2
(45) Date of Patent: May 5, 2015

(54) BROMINATED FLAME RETARDANT DETERMINING METHOD, BROMINATED FLAME RETARDANT DETERMINING APPARATUS, RECYCLING METHOD, AND RECYCLING APPARATUS

(75) Inventors: Kenichiro Mase, Osaka (JP); Sadafumi Oota, Osaka (JP); Masatoshi Miyasaka, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 402 days.

(21) Appl. No.: 13/579,115

(22) PCT Filed: Sep. 16, 2011

(86) PCT No.: PCT/JP2011/005256
§ 371 (c)(1),
(2), (4) Date: Aug. 15, 2012

(87) PCT Pub. No.: WO2012/035785
PCT Pub. Date: Mar. 22, 2012

(65) Prior Publication Data
US 2012/0305456 A1     Dec. 6, 2012

(30) Foreign Application Priority Data
Sep. 17, 2010 (JP) .................. 2010-208909

(51) Int. Cl.
*B07C 5/342* (2006.01)
*G01N 21/3563* (2014.01)
(Continued)

(52) U.S. Cl.
CPC ............ *G01N 21/3563* (2013.01); *B07C 5/342* (2013.01); *G01N 21/85* (2013.01);
(Continued)

(58) Field of Classification Search
CPC .............. B07C 5/342; G01N 21/3563; G01N 2201/0618; G01N 2201/129; G01J 2003/425; G01J 3/28
USPC ................. 209/576, 587, 930; 356/302, 303; 250/339.01, 339.08, 341.8
See application file for complete search history.

(56) References Cited

U.S. PATENT DOCUMENTS 5,134,291 A * 7/1992 Ruhl et al. ............... 250/339.11
5,448,070 A * 9/1995 Day et al. ................. 250/339.13
(Continued)

FOREIGN PATENT DOCUMENTS

JP    2005-283336    10/2005
JP    2007-271352    10/2007
(Continued)

OTHER PUBLICATIONS

International Search Report issued Dec. 6, 2011 in International (PCT) Application No. PCT/JP2011/005256.
(Continued)

*Primary Examiner* — Joseph C Rodriguez
(74) *Attorney, Agent, or Firm* — Wenderoth, Lind & Ponack, L.L.P.

(57) ABSTRACT

The present invention provides a brominated flame retardant determining method that determines whether or not a brominated flame retardant is contained in a determination target object by emitting light to the determination target object composed of resin, receiving reflected light from the determination target object emitted with the light, calculating an absorption spectrum of the determination target object based on the reflected light, and determining whether or not a brominated flame retardant is contained in the determination target object in the absorption spectrum, based on an absorption spectrum in a wavelength band of 1.40 μm or more and 2.50 μm or less.

14 Claims, 14 Drawing Sheets

(51) Int. Cl.
  B29B 17/02 (2006.01)
  G01N 21/359 (2014.01)
  G01J 3/42 (2006.01)
  G01J 3/02 (2006.01)
  G01N 21/85 (2006.01)
  G01N 21/94 (2006.01)
  B29K 55/02 (2006.01)
  B29K 105/00 (2006.01)

(52) U.S. Cl.
  CPC ............ B29B 17/02 (2013.01); G01N 21/359 (2013.01); G01N 21/94 (2013.01); G01N 2201/0618 (2013.01); G01N 2201/129 (2013.01); G01J 3/42 (2013.01); G01J 3/0218 (2013.01); B29K 2055/02 (2013.01); B29K 2105/0026 (2013.01); B29B 2017/0203 (2013.01); B29B 2017/0279 (2013.01)

(56) References Cited

U.S. PATENT DOCUMENTS

| | | | |
|---|---|---|---|
| 5,952,660 | A | 9/1999 | Kip et al. |
| 6,555,822 | B1 * | 4/2003 | Zoidis .................. 250/341.1 |
| 7,271,388 | B2 * | 9/2007 | Riess et al. ............. 250/341.8 |
| 7,483,124 | B2 * | 1/2009 | Saito ......................... 356/38 |
| 8,812,149 | B2 * | 8/2014 | Doak ......................... 700/223 |
| 2007/0229800 | A1 * | 10/2007 | Saito ......................... 356/36 |
| 2011/0108739 | A1 * | 5/2011 | Hanko ..................... 250/459.1 |

FOREIGN PATENT DOCUMENTS

| | | |
|---|---|---|
| JP | 2008-39680 | 2/2008 |
| JP | 2010-207772 | 9/2010 |

OTHER PUBLICATIONS

Japanese Office Action issued Mar. 12, 2013 in Japanese Patent Application No. 2012-504988.
Keith Freegard et al., "Develop a process to separate brominated flame retardants from WEEE polymers—Final Report", [ISBN: 1-84405-315-6], The Waste & Resources Action Programme, pp. 1-2, 12-15, 60-64, and 81-83, Nov. 2006.
M. Robben et al., "NIR Spectral Imaging in the Minerals Industry", 15 Workshop Farbbildverarbeitung 2009, 8p, Oct. 2009.
Chinese Office Action issued Jul. 25, 2014 in corresponding Chinese Patent Application No. 201180008288.1 (with English translation).
English translation of the International Preliminary Report on Patentability issued Apr. 25, 2013 in International (PCT) Application No. PCT/JP2011/005256.
Extended European Search Report issued Mar. 25, 2014 in corresponding European Patent Application No. 11824798.0.
A.K. Bledzki et al., "Rapid Identification of Plastics in Recycling Processes", International Polymer Science and Technology, Rapra Technology, Shrewabury, GB, vol. 25, No. 4, 1998, pp. T90-T96, XP000803325, ISSN: 0307-174X.
Raimund Leitner et al., "Real-time Detection of Flame-Retardant Additives in Polymers and Polymer Blends with NIR Imaging Spectroscopy", Proceedings of SPIE, vol. 7312, Apr. 30, 2009, pp. 73120M-73120M-9, XP055107715, ISSN: 0277-786X, DOI: 10.1117/12.818540.

* cited by examiner

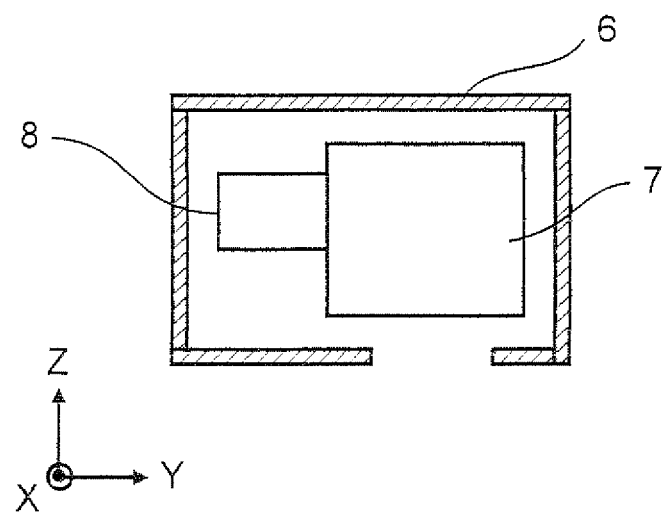

BROMINATED FLAME RETARDANT DETERMINING METHOD, BROMINATED FLAME RETARDANT DETERMINING APPARATUS, RECYCLING METHOD, AND RECYCLING APPARATUS

TECHNICAL FIELD

The present invention relates to brominated flame retardant determining method and apparatus each for determining whether or not a brominated flame retardant is contained in resin, a recycling method, and a recycling apparatus.

BACKGROUND ART

Due to economic activities based on mass consumption and mass disposal, there are global environmental problems such as global warming or resource depletion.

Under the circumstances, aiming at structuring the resource recycling-based society, The Home Appliance Recycling Law has been in effect since April 2001 in Japan. Under The Home Appliance Recycling Law, it is mandatory to recycle used home appliances (air conditioners, television sets, refrigerators, freezers, washing machines, cloth driers and the like).

Therefore, used home appliances are crushed, and thereafter selectively separated and collected for each material using magnetism, wind power, vibration, or the like at home appliance recycling factories, and recycled as recycled materials.

Further, "Restriction of the use of certain Hazardous Substances (RoHS directive, for short)" which has been in effect since July 2006 by the European Union (EU) restricts use of polybrominated biphenyl (PBB) or polybrominated diphenyl ether (PBDE) for home appliances.

Some types of resin used for home appliances contain a bromine compound such as PBB, PBDE, or the like as a flame retardant order to possess flame retardancy.

Products using resin containing such compounds as a recycled material are restricted under the RoHS directive.

Further, in some cases, bromine compounds other than PEE or PBDE are also added to resin as a flame retardant. In the following, any bromine compound such as PBB or PBDE added as a flame retardant will be referred to as a brominated flame retardant.

Though there are some brominated flame retardants not restricted under the RoHS directive, from the viewpoint of environmental protection, it is preferable that resin as a recycled material does not contain any brominated flame retardant.

Accordingly, it has been necessary to determine whether or not the resin being a recycled material contains a brominated flame retardant.

Conventionally, as a method for detecting a brominated flame retardant contained in resin being a recycled material, Fourier transform infrared spectrophotometric method (FT-IR), which is disclosed by Japanese Unexamined Patent Publication No. 2005-283336, for example, is used.

FIG. 11 shows a brominated flame retardant determining apparatus 100 that uses the conventional FT-IR. A measurement data storage unit 102 is to store absorption spectra of mid infrared light (wavelength band 2.5 to 25 µm, wave number range 400 to 4000 cm$^{-1}$) obtained by a measuring apparatus 101. A reference data storage unit 103 is to store previously obtained reference data. A peak detecting unit 104 is to read a measured absorption spectrum from the measurement data storage unit 102, and detect the peak thereof based on a prescribed reference, to obtain the wave number and intensity thereof. A reference data acquiring unit 105 is to acquire reference data pieces in a prescribed order according to the control exerted by a control unit 106. A determining unit 107 is to compare the acquired measured data and the reference data against each other to determine whether or not a determination target object contains a brominated flame retardant. An input unit 108 is to receive measurement conditions, analysis conditions, and the like from the user.

The brominated flame retardant determining apparatus 100 using the conventional FT-IR analyzes the absorption spectrum of the mid infrared light of the transmitted light or reflected light from the resin, to thereby determine whether or not a brominated flame retardant is contained in the resin.

CITATION LIST

Patent Literature

[Patent Literature 1] Japanese Unexamined Patent Publication No. 2005-283336

SUMMARY OF INVENTION

Technical Problem

However, in a case where the FT-IR is used to determine whether or not a brominated flame retardant is contained, the light quantity required for determining resin cannot be obtained unless preprocessing such as ATR (attenuated total reflection) measurement is performed. Therefore, it is difficult to determine whether or not a brominated flame retardant is contained by applying FT-IR to recycling steps, which requires fast-speed determination of a plurality of determination target objects.

Accordingly, in consideration of such problems, an object of the present invention is provide a brominated flame retardant determining method and apparatus, a recycling method, and a recycling apparatus, each detecting a brominated flame retardant contained in resin at high speeds to determine whether or not the resin contains the brominated flame retardant.

Solution to Problem

In order to achieve the object stated above, the present invention is structured as follows.

According to one aspect of the present invention, there is provided a brominated flame retardant determining method, comprising:

emitting light to a determination target object composed of resin;

receiving reflected light from the determination target object emitted with the light;

calculating an absorption spectrum of the determination target object based on the reflected light; and determining whether or not a brominated flame retardant is contained in the determination target object based on, in the absorption spectrum, an absorption spectrum in at least one of wavelength bands including a wavelength band of 1.42 µm or more and 1.44 µm or less, a wavelength band of 1.45 µm or more and 1.47 µm or less, a wavelength band of 1.66 µm or more and 1.68 µm or less, a wavelength band of 1.72 µm or more and 1.74 µm or less, a wavelength band of 1.92 µm or more and 1.94 µm or less, a wavelength band of 2.11 µm or more and 2.12 µm or less, a wavelength band of 2.17 µm or more and 2.20 µm or less, and a wavelength band of 2.31 µm or more and 2.34 µm or less.

According to other aspect of the present invention, there is provided a recycling method, comprising:

conveying a plurality of determination target objects each composed of resin;

thereafter, applying the brominated flame retardant determining method according to the foregoing aspect to the conveyed determination target objects; and thereafter, selectively separating the determination target objects into a determination target object determined to be containing a brominated flame retardant and a determination target object determined to be free of the brominated flame retardant, to thereby reuse the determination target object determined to be free of the brominated flame retardant.

According to other aspect of the present invention, there is provided a brominated flame retardant determining apparatus, comprising:

an emission unit that emits light to a determination target object composed of resin;

a light receiving unit that receives reflected light from the determination target object emitted with the light; and an arithmetic processing unit that calculates an absorption spectrum of the determination target object based on the reflected light, wherein the arithmetic processing unit determines whether or not a brominated flame retardant is contained in the determination target object based on, in the absorption spectrum, an absorption spectrum in at least one of wavelength bands including a wavelength band of 1.42 μm or more and 1.44 μm or less, a wavelength band of 1.45 μm or more and 1.47 μm or less, a wavelength band of 1.66 μm or more and 1.68 μm or less, a wavelength band of 1.72 μm or more and 1.74 μm or less, a wavelength band of 1.92 μm or more and 1.94 μm or less, a wavelength band of 2.11 μm or more and 2.12 μm or less, a wavelength band of 2.17 μm or more and 2.20 μm or less, and a wavelength band of 2.31 μm or more and 2.34 μm or less.

According to other aspect of the present invention, there is provided a recycling apparatus, comprising:

a conveying unit that conveys a plurality of determination target objects each composed of resin;

the brominated flame retardant determining apparatus according to the foregoing aspect; and a selectively separating unit that selectively separates the determination target objects into a determination target object determined to be containing a brominated flame retardant and a determination target object determined to be free of the brominated flame retardant.

Advantageous Effects of Invention

The present invention can achieve high-speed determination as to whether or not a brominated flame retardant is contained in a determination target object.

BRIEF DESCRIPTION OF DRAWINGS

These and other aspects and features of the present invention will become clear from the following description taken in conjunction with the preferred embodiments thereof with reference to the accompanying drawings, in which:

FIG. 2 is a schematic view showing the schematic structure of a near infrared light detecting device of the brominated flame retardant determining apparatus according the first embodiment of the present invention;

DESCRIPTION OF EMBODIMENTS

Figure 1A:
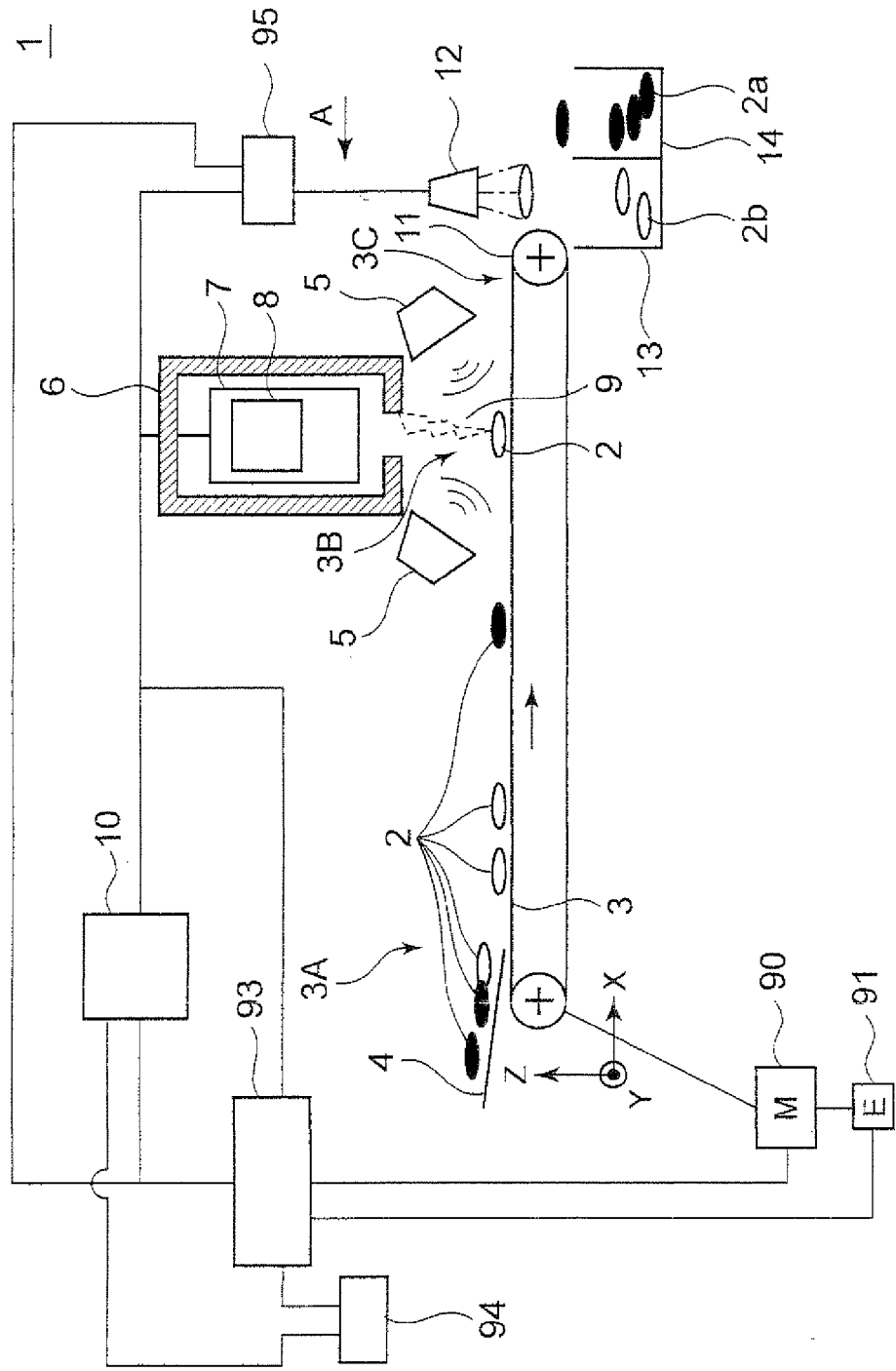
FIG. 1A is a schematic view of a brominated flame retardant determining apparatus according to a first embodiment of the present invention.

In the following, with reference to the drawings, a description will be given of embodiments of the present invention. It is to be noted that, in the following description, identical structures are denoted by identical reference characters, and a description thereof will not be repeated.

First Embodiment

FIG. 1A is a schematic view of a brominated flame retardant determining apparatus 1 according to a first embodiment.

Determination target objects 2 are each resin whether or not it contains a brominated flame retardant is unknown. With reference to FIG. 1A, a description will be given of the structure of a brominated flame retardant determining apparatus 1 that detects a brominated flame retardant from the determination target objects 2.

The brominated flame retardant determining apparatus 1 includes halogen lamps 5 each being one example of an emission unit that emits light to the determination target objects 2 composed of resin, a near infrared light detecting device 6 that has a light receiving unit that receives reflected light 9 from the determination target objects 2 having been emitted with the light, and an arithmetic processing device (arithmetic processing unit) that calculates the absorption spectra of the determination target objects 2 based on the reflected light 9.

In FIG. 1A, a conveyer belt 3 is one example of a conveying unit that moves at a constant speed to convey the determination target objects 2. This conveyer belt 3 conveys the determination target objects 2 from an input region 3A to a selectively separating region 3C via a detection region 3B along the longitudinal direction of the conveyer belt 3. A hopper 4 is one example of an input unit that inputs the determination target objects 2 onto the conveyer belt 3. The vibration or swinging of the hopper 4 successively inputs the determination target objects 2 on the hopper 4 to the input region 3A at one end on the conveyer belt 3.

A pair of halogen lamps 5 arranged above the detection region 36 of the conveyer belt 3 is an example of an emission unit that emits light including near infrared light (the light whose wavelength band is 1.40 μm and more to 2.50 μm or less) to the determination target objects 2.

Further, above the detection region 3B of the conveyer belt 3, the near infrared light detecting device 6 that has the light receiving unit that receives reflected light from the determination target objects 2 is arranged. The near infrared light detecting device 6 is a device that includes a near infrared light scanning unit 7 and a near infrared light detecting unit 8 whose description will follow. The near infrared light detecting device 6 is to receive the reflected light 9 from the determination target objects 2 having been emitted with the light by the halogen lamps 5, and to output information of the received reflected light 9 to the arithmetic processing unit 10.

The arithmetic processing unit 10 is to analyze the information outputted from the near infrared light detecting device 6 and to obtain the absorption spectra of the determination target objects 2. Further, the arithmetic processing unit 10 is to detect a brominated flame retardant by evaluating the absorption spectra. Still further, the arithmetic processing unit 10 is to determine a determination target object 2 from which a brominated flame retardant is detected to be a determination target object 2a containing a brominated flame retardant, and to determine a determination target object 2 from which no brominated flame retardant is detected to be a determination target object 2b containing no brominated flame retardant A pulse air nozzle 12 and an air supply source 95 installed above a terminal portion 11 being the selectively separating region 3C of the conveyer belt 3 serve as an example of a selectively separating unit that blows air to the determination target objects 2b. Based on the instructions from the arithmetic processing unit 10 or a control unit 93, the air supply source 95 is driven, and air in an amount corresponding to a drive amount of the air supply source 95 is blown from the pulse air nozzle 12, to selectively separate the determination target objects 2a and the determination target objects 2b.

A recycle box 13 is to store the determination target objects 2b that are determined to be containing no brominated flame retardant. A disposal box 14 is to store the determination target objects 2a that is determined to be containing the brominated flame retardant.

The determination target object 2b determined to be containing no brominated flame retardant is blown by air from the pulse air nozzle 12 and falls so as to forcibly deviate from the path of free fall, and is stored in the recycle box 13. The determination target object 2a to which air is not blown from the pulse air nozzle 12 passes over the recycle box 13 by free fall from the terminal portion 11 of the conveyer belt 3, and is stored in the disposal box 14. The positional information of the determination target object 2 is specified by a position calculation unit 94 connected to the control unit 93. Specifically, the position of the determination target object 2 on the conveyer belt 3 is specified by the position calculation unit 94 by the value from an encoder detector 91 attached to a motor 90 of the conveyer belt 3 controlled by the control unit 93, and the arrangement position of the light receiving unit of the near infrared light detecting device 6.

Next, a description will be given of the near infrared light scanning unit 7 and the near infrared light detecting unit 8 included in the near infrared light detecting device 6. FIG. 2 is a schematic view showing the schematic structure of the near infrared light detecting device 6 as seen from the direction of arrow A shown in FIG. 1A. As shown in FIG. 2, the near infrared light detecting device 6 includes the near infrared light scanning unit and the near infrared light detecting unit 8. The near infrared light scanning unit 7 is to scan in the width direction of the conveyer belt 3, to thereby cause the reflected light 9 at each scanning position on the conveyer belt 3 to enter the near infrared light detecting unit 8. The near infrared light detecting unit 8 is to receive the reflected light 9 entered from the near infrared light scanning unit 7.

Figure 3:
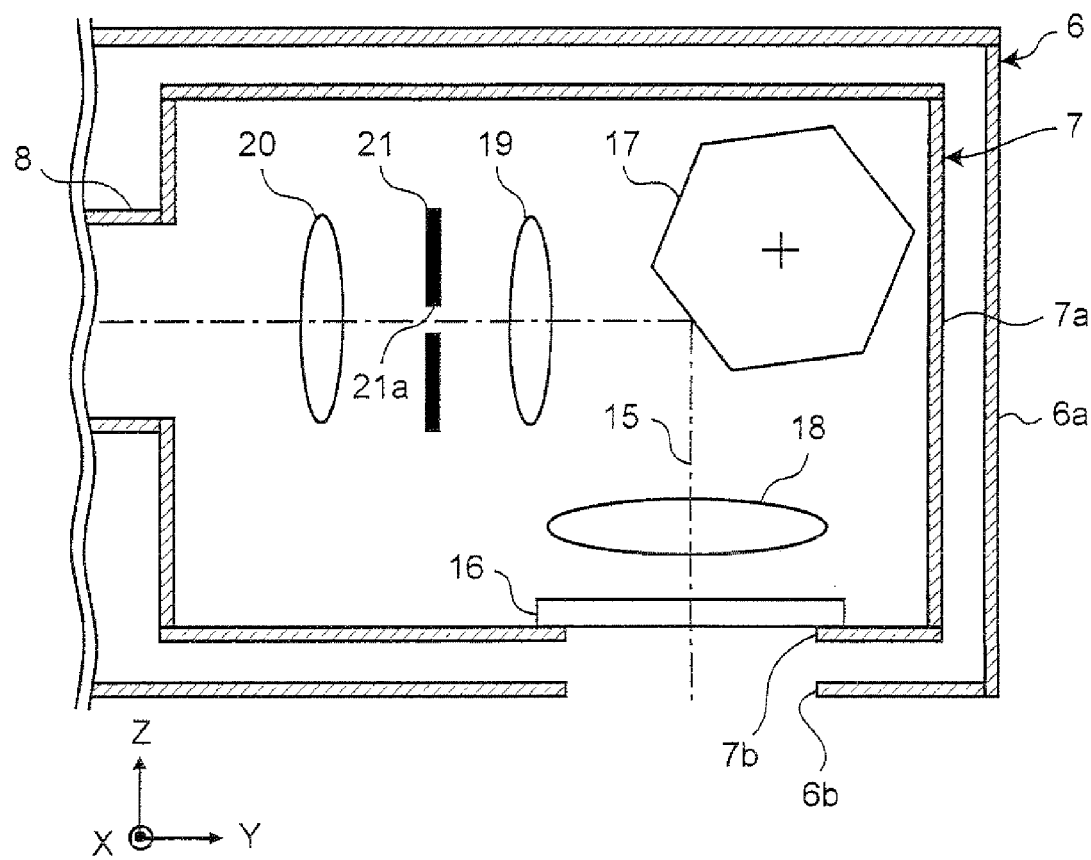
FIG. 3 is a schematic view of a near infrared light scanning unit included in the near infrared light detecting device of the brominated flame retardant determining apparatus according to the first embodiment of the present invention.

First, with reference to FIG. 3, a description will be given of the structure of the near infrared light scanning unit 7. FIG. 3 is a partial schematic view of the brominated flame retardant determining apparatus 1 shown in FIG. 1A as seen from the conveying direction (the direction of arrow A shown in FIG. 1A) of the conveyer belt 3. FIG. 3 shows the near infrared light scanning unit 7 arranged inside a frame member 6a of the near infrared light detecting device 6. The alternate long and short dash line shown in FIG. 3 represents an optical axis 15 of the reflected light 9. The near infrared light scanning unit 7 includes a wavelength filter 16, an fθ lens 18, a polygon rotary mirror 17, a condenser lens 19, an aperture 21 as an example of an opening restriction member, and a condenser lens 20.

The wavelength filter 16 is to allow transmission of only the light of a wavelength band of 1.40 μm or more and 2.50 μm or less included in the reflected light 9 that enters the near infrared light scanning unit 7 via an opening 6b of the frame member 6a of the near infrared light detecting device 6 and an opening 7b of the frame member 7a of the near infrared light scanning unit 7. By the wavelength filter 16, only the near infrared light included in the reflected light 9 enters the near infrared light scanning unit 7.

The polygon rotary mirror 17 is rotated by a rotary drive device such as a motor, to enable scanning in the width direction of the conveyer belt 3, and to enable detection of the reflected light 9 at each scanning point on the conveyer belt 3.

The fθ lens 18 arranged between the wavelength filter 16 and the polygon rotary mirror 17 is a lens that has the fθ function that equalizes the difference in the scanning speed between the center of the polygon rotary mirror 17 and the periphery thereof.

The condenser lens 19 is a lens that condenses the reflected light 9 reflected from the polygon rotary mirror 17.

The condenser lens 20 is a lens that converts the reflected light 9 having been condensed by the condenser lens 19 into collimated light, and allows the collimated light to enter the near infrared light detecting unit 8, whose description will follow.

The aperture 21 whose opening 21a is arranged at the focal point of the condenser lens 19 and the condenser lens 20 is an opening restriction member that restricts the opening such that light in the area other than each scanning point on the conveyer belt 3 does not enter.

Figure 4:
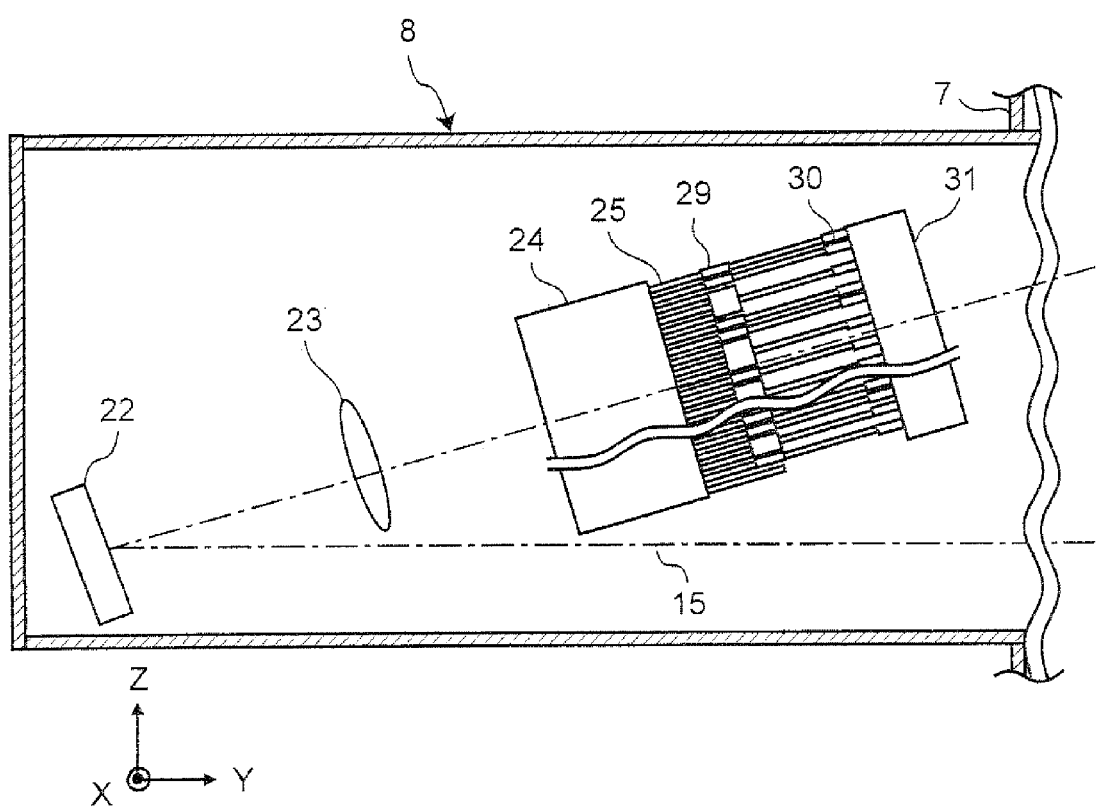
FIG. 4 is a schematic view of the near infrared light detecting unit included in the near infrared light detecting device of the brominated flame retardant determining apparatus according to the first embodiment of the present invention.

Next, with reference to FIGS. 4 and 5, a description will be given of the structure of the near infrared light detecting unit 8. FIG. 4 is a schematic view of the structure of the near infrared light detecting unit 8 arranged inside the near infrared light detecting device 6 shown in FIG. 2. The near infrared light detecting unit 8 includes a diffraction grating 22, a condenser lens 23, a light receiving array 24 as one example of a light receiving unit, optical fibers 25, connectors 29, light receiving elements 30, and a digital data converting device 31.

The diffraction grating 22 is one example of a spectroscopic unit that allows the reflected light 9 entered from the near infrared light scanning unit 7 shown in FIG. 3 to reflectively diffract, to thereby disperse the reflected light 9 for each wavelength band at its corresponding angle. In the first embodiment, as one example, the diffraction grating 22 is installed as being tilted by 35 degrees relative to the optical axis 15 of the reflected light 9 outputted from the condenser lens 20. This angle is set in order to avoid mechanical interference and to separate the 0th order light of direct reflection and the 1st order diffracted light from each other. As the diffraction grating 22, a plane blazed diffraction grating is employed with emphasis on the diffraction efficiency.

The condenser lens 23 is a lens that condenses the reflected light 9 dispersed by the diffraction grating 22 for each wavelength band.

The light receiving array 24 is one example of a light receiving unit that receives the reflected light 9 condensed by the condenser lens 23 and having been dispersed for each wavelength band.

Figure 5:
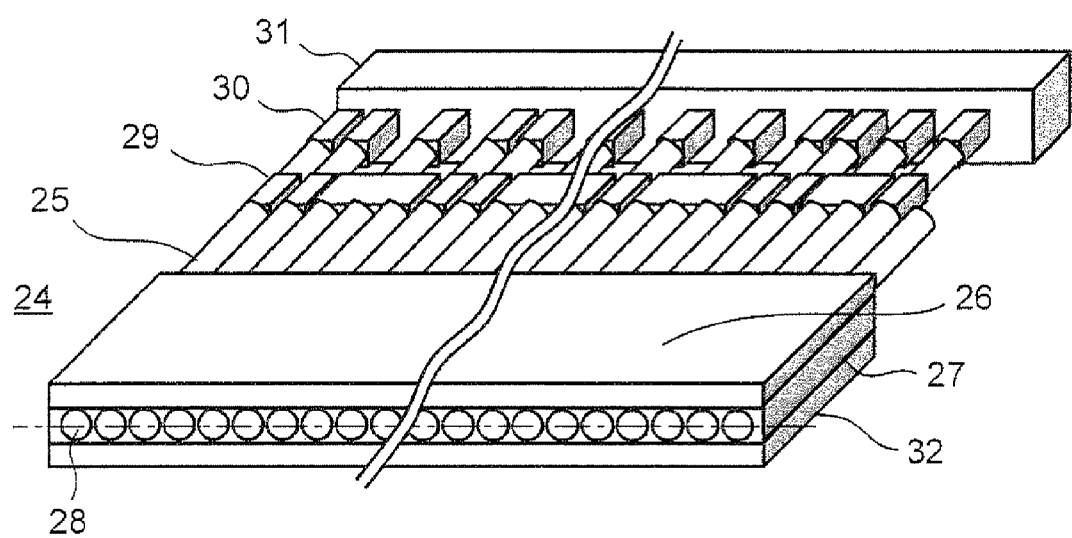
FIG. 5 is a schematic view of a light receiving array of the brominated flame retardant determining apparatus according to the first embodiment of the present invention.

FIG. 5 is a schematic view showing the structure of the light receiving array 24. The light receiving array 24 is structured such that a plurality of optical fibers 25 are aligned in one row as being sandwiched between a top face plate 26 and a bottom face plate 27. The top face plate 26 and the bottom face plate 27 are each made of glass. At the bottom face plate 27, grooves that respectively conform to the shape of a plurality of optical fibers 25 are formed. An end face 28 of every optical fiber 25 sandwiched between the bottom face-plate 27 and the top face plate 26 and fixedly bonded between the bottom face plate 27 and the top face plate 26 is polished, and the end face 28 serves as the light receiving surface. Here, as one example, the number of the optical fibers 25 included in the light receiving array 24 is 110. The light entered from each end face 28 is guided inside the optical fiber 25, and is photoelectrically converted at the light receiving element 30 via the connector 29 coupled to the other end of the optical fiber 25. The signal of the photoelectrically converted current is converted into digital data by the digital data converting device 31 that includes an optical gain current-to-voltage converting amplifier and a high-speed A/D converter circuit. Further, as one example, quartz is used as the core of each optical fiber 25, and the core diameter is 500 μm, and the cladding diameter is 600 μm. In this case, the straight line that passes the center of each end face 28 is defined as a horizontal optical axis reference 32.

The reflected light 9 dispersed for each wavelength band is condensed by the condenser lens 23 on the horizontal optical axis reference 32 on the end face 28 at the light receiving array 24. The diffraction grating 22 and the light receiving array 24 are installed such that the beams of dispersed reflected light 9 on the shorter wavelength side enter the optical fibers 25 positioned on the upper side in FIG. 4, and those on the longer wavelength side enter the optical fibers 25 positioned on the bottom side in FIG. 4. Thus, the optical fibers 25 respectively receive light beams of different wavelengths.

Here, the optical fiber 25 that receives the shortest wavelength light out of the dispersed reflected light 9 entering the light receiving array 24 and that is arranged at the top end is referred to as 1 channel, and the optical fiber 25 that receives the longest wavelength light thereof and that is arranged at the bottom end is referred to as 110 channel. In this case, by the wavelength filter 16, since the wavelengths of the beams of reflected light 9 is limited to the wavelength band of 1.40 μm or more and 2.50 μm or less, when the wavelengths are taken by 110 pieces of optical fibers 25, the wavelength band detected per one channel, i.e., the resolution of the light receiving array 24, becomes 0.01 μm. Specifically, the wavelength bands are evenly allotted such that light of the wavelength band of 1.40 μm or more and 1.41 μm or less enters 1 channel, that of 1.41 μm or more and 1.42 μm or less enters 2 channel, . . . , that of 2.48 μm or more and 2.49 μm or less enters 109 channel, and that of 2.49 μm or more and 2.50 μm or less enters 110 channel.

In this case, it is set such that the wavelength positioned at the boundary of the channels is detected by either one of the channels. For example, when the dispersed reflected light 9 of the wavelength including 1.41 μm and equal to or shorter than 1.41 μm is detected at 1 channel, it is set such that the wavelength exceeding 1.41 μm and longer than 1.41 μm is detected at 2 channel, to thereby prevent the wavelength positioned at the boundary of the 1 channel and 2 channel (in this case, the wavelength of 1.41 μm) from being detected as being overlapped by those channels. The reflected light 9 dispersed for each wavelength band and entering each optical fiber 25 is photoelectrically converted by the light receiving element 30, and the signal of the photoelectrically converted current is converted into digital data by the digital data converting device 31. The digital data is inputted to the arithmetic processing unit 10 shown in FIGS. 1A and 1B, and the arithmetic processing unit 10 analyzes the received digital data to obtain the absorption spectra of the determination target object 2.

Here, with reference to FIGS. 1A and 4, a brief description will be given of the arithmetic processing unit performing a method for calculating the absorption spectrum from the received digital data. The electric signal photoelectrically converted by the light receiving element 30 shown in FIG. 4 is dependent on the intensity of received light. Accordingly, it is possible to obtain information of the intensity of the light for each wavelength band from the digital data converted by the digital data converting device 31. From the information of the intensity of light for each of the obtained wavelength bands, the absorbance for each wavelength band of the determination target object 2 is calculated. From the calculated absorbance for each wavelength band, the absorption spectrum of the determination target object 2 can be obtained. The arithmetic processing unit 10 evaluates the absorption spectrum to thereby detect a brominated flame retardant, and determines whether or not the determination target object 2 contains the brominated flame retardant.

Here, a description will be given of near infrared spectroscopy using near infrared light (the light whose wavelength is 2.5 μm or less) prior to describing the method for detecting a brominated flame retardant according to the first embodiment.

First, the principle of the near infrared light being absorbed by a substance will be described.

Two molecules bonded by covalent bond vibrate while maintaining the equilibrium distance. This vibration includes a variety of vibration modes such as stretching vibration in which the bonding distance between the molecules increases and reduces, bending vibration in which the bonding angle vibrates, or internal rotation vibration in which vibration occurs about the bonding axis. Such vibrations each having an independent vibration characteristic are referred to as normal vibrations. Among normal vibrations, interaction among vibrations occurs due to the anharmonicity of the vibrations. Thus, dipole moment changes and, then, absorption of near infrared light occurs.

The wavelength of the absorbed near infrared light and the extent of absorption (absorbance) is determined by the type of substance. Accordingly, the absorption spectrum when near infrared light is emitted shows the high position (peak) of absorbance at a particular wavelength band. That is, by evaluating the peak of the absorption spectrum, the substance can be specified.

With an organic and macromolecular compound such as resin, absorption of near infrared light by C—H base bond can be seen as the peak of the absorption spectrum. For example, ABS (acrylonitrile butadiene styrene copolymerization composition) resin has a peak of absorption spectrum around 1.96 μm attributed to the molecular structure contained in acrylonitrile. Further, PP resin (polypropylene resin) has a peak of absorption spectrum also around 1.75 μm attributed to the $CH_3$ content.

In this manner, by emitting near infrared light to detect the peak of absorption spectrum, the type of resin can be determined.

However, emission of near infrared light cannot detect the peak of absorption spectrum attributed to anharmonicity from C—Br (carbon-bromine) bond. Accordingly, it is impossible to detect bromine itself by using near infrared light. Then, the inventors found a method for detecting a brominated flame retardant using near infrared light instead of directly detecting the absorption spectrum of bromine, i.e., a method of detecting a brominated flame retardant according to the first embodiment.

Next, a description will be given of the principle of the method of detecting a brominated flame retardant using the brominated flame retardant determining apparatus 1.

As brominated flame retardants in worldwide use, there are bromine compounds such as tetrabromobisphenol-based or hexabromocyclododecane-based. Many of these brominated flame retardants are of the type having a molecular structure having not only C—Br bond but also C—H bond. The absorption of the near infrared light attributed to the C—H bond that is present near C—Br bond will be affected by the enharmonic vibration attributed to the C—Br bond. That is, it is considered that the C—H bond absorbs near infrared light under the effect of not only the inherent stretching vibration and bending vibration of the C—H bond, but also the C—Br bond that is present nearby. Accordingly, if a peak of the absorption spectrum of C—H bond occurs as being shifted from the wavelength where the inherent peak of absorption spectrum appears, then the presence of C—Br bond can be determined based on that the shift is attributed to the effect of C—Br bond. That is, the inventors have arrived at the idea that, by detecting the absorption spectrum of C—H bond and evaluating whether or not the peak position is shifted, it can be detected whether or not a brominated flame retardant is present.

Next, a description will be given of a result of an experiment that was carried out based on the principle the method for detecting a brominated flame retardant according to the first embodiment.

Figure 6:
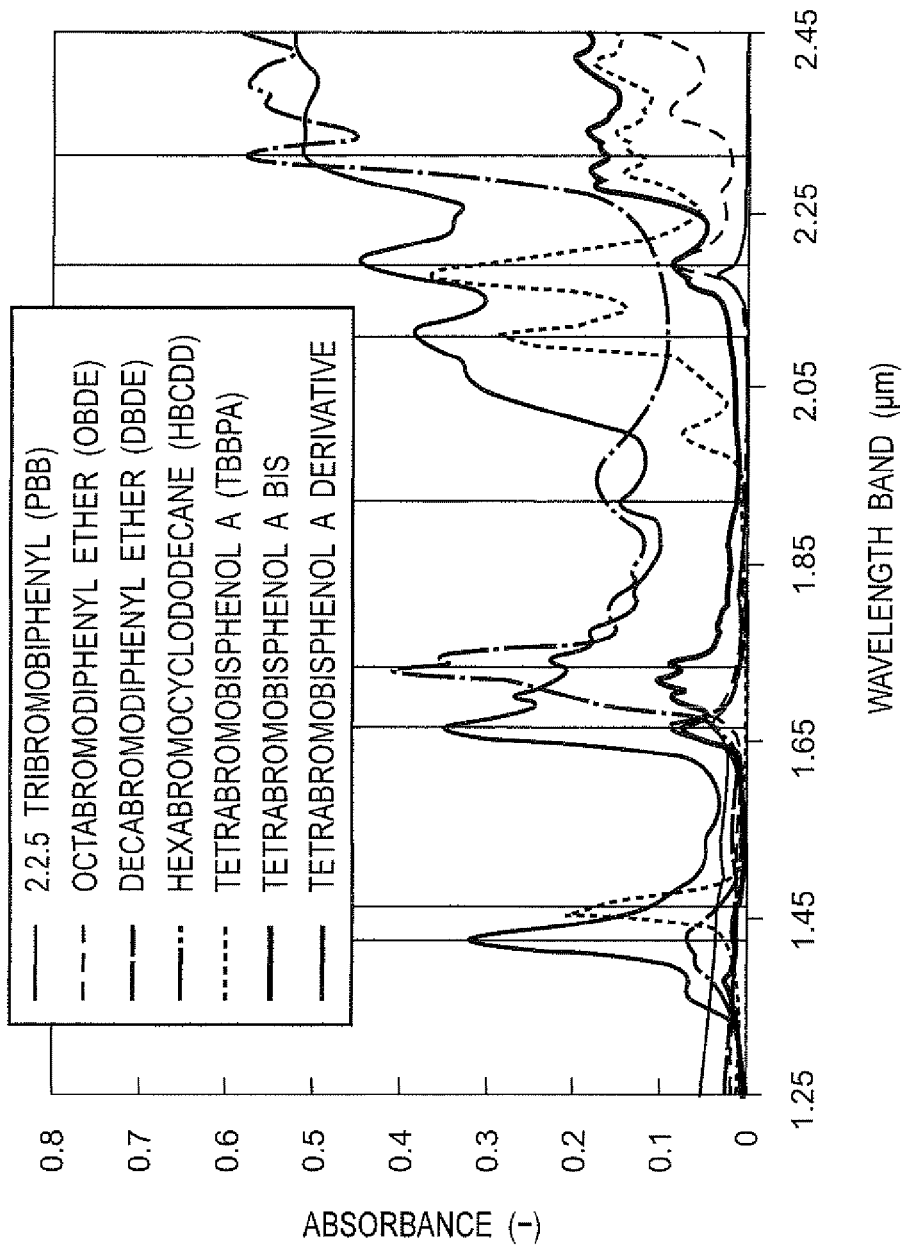
FIG. 6 is a graph of absorption spectra of brominated flame retardants determined according to the first embodiment of the present invention.

The absorption spectra when near infrared light was emitted to seven bromine compounds (brominated flame retardants) were obtained. Namely, the seven bromine compounds as major brominated flame retardants added to resin were: 2.2.5 tribromobiphenyl (PBB) being one example of PBB; octabromodiphenyl ether (OBDE); decabromodiphenyl ether (DBDE); hexabromocyclododecane (HBCDD); tetrabromobisphenol A (TBBPA); tetrabromobisphenol A bis (TBBPA-bis); and a tetrabromobisphenol A derivative (TBBPA derivative). It is to be noted that OBED and DBDE are each one type of PBDE. FIG. 6 is a graph showing the absorption spectra of these brominated flame retardants. In the graph of FIG. 6, the horizontal axis indicates wavelength band and the vertical axis represents absorbance. From the result shown in FIG. 6, it can be verified that a characteristic peak of an absorption spectrum exists for each type of the brominated flame retardant.

The peaks of the absorption spectra detected herein are mostly attributed to C—H bond which is affected by C—Br bond. That is, it is considered that the peaks of the absorption spectra of C—H bond detected herein are shifted from the inherent peak position of the absorption spectrum of C—H bond.

Figure 7:
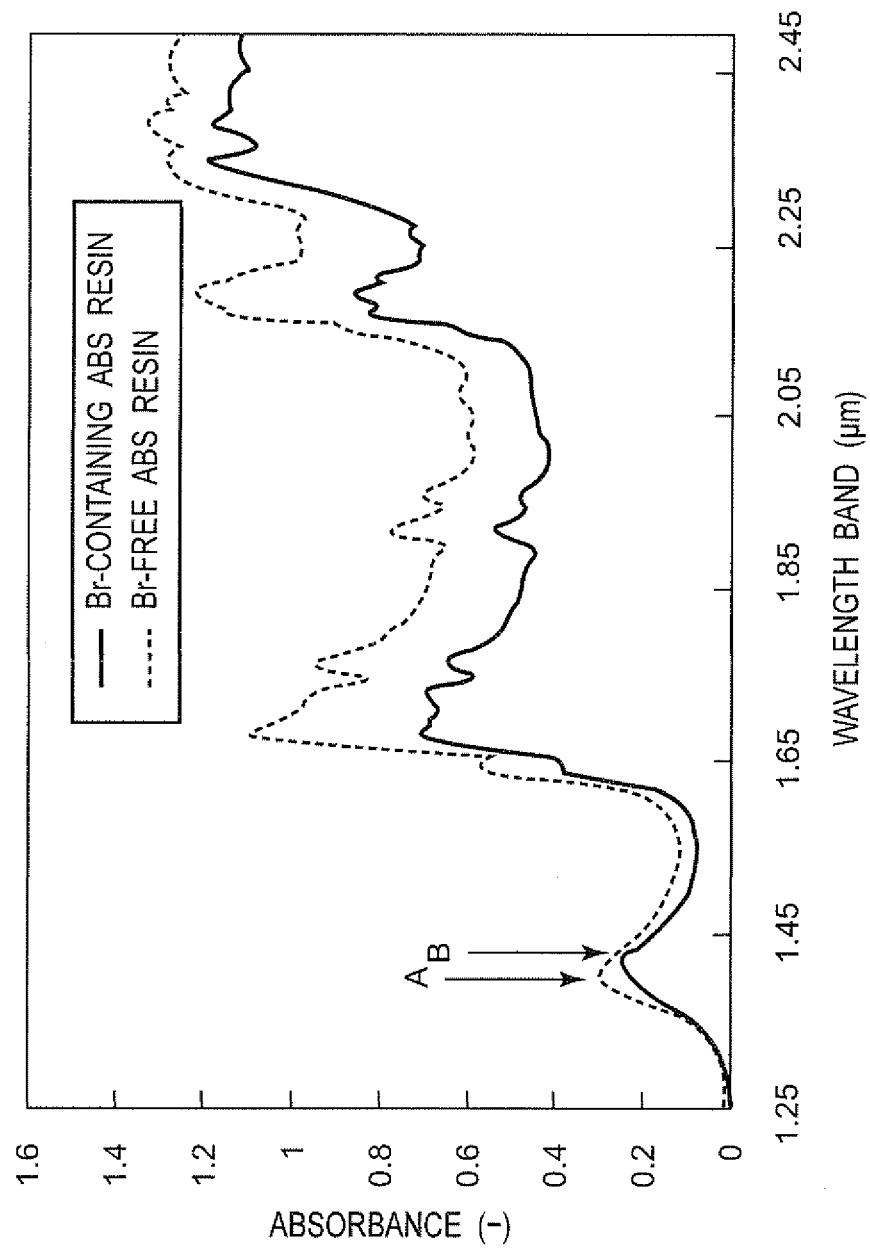
FIG. 7 is a graph of absorption spectra of ABS resin containing no brominated flame retardant and ABS resin containing a brominated flame retardant.

Next, an experiment was carried out as to whether or not a peak of an absorption spectrum being shifted from the inherent position of the peak of the absorption spectrum of C—H bond can be seen also from a brominated flame retardant contained in resin. Here, absorption spectrum measurements of ABS resin not containing a brominated flame retardant (hereinafter referred to as the Br-free ABS resin) and that of ABS resin containing a brominated flame retardant (hereinafter referred to as the Br-containing ABS resin) were compared against each other. For the experiment, as the Br-containing ABS resin, ABS resin whose content of a tetrabromobisphenol A derivative-base flame retardant was 10% (mass fraction) was used. The result of measured absorption spectra is shown in FIG. 7. At the position (1.41 μm) indicated by arrow A and at the position (1.43 μm) indicated by arrow B shown in FIG. 7, it can be seen that a peak of the Br-free ABS resin and a peak of the Br-containing ABS resin are present differing from each other, though the difference is of a slight amount.

The Br-containing ABS resin contains ABS resin whose proportion is reduced by the proportion of the content of the brominated flame retardant. Therefore, as compared to the absorbance of the Br-free ABS resin, the absorbance of the Br-containing ABS resin becomes smaller as a whole. However, it is not likely that the peak position of the absorption spectrum shifts because of a reduction in the content of ABS resin. That is, it is considered that, as described above, the occurrence of the different peaks at the position of arrow A and the position of arrow B is caused by the peak of the absorption spectrum part of C—H bonds shifting from the theoretical peak position (1.41 μm) to the experimentally obtained peak position (1.43 μm) which is attributed to the contained brominated flame retardant. Based on the foregoing, the inventors have arrived at the idea that evaluation of the absorption spectrum of 1.43 μm makes it possible to detect a brominated flame retardant, and to determine whether or not a brominated flame retardant is contained in ABS resin.

In this case, the position (1.43 μm) of arrow B substantially matches with the peak position of the tetrabromobisphenol A derivative in FIG. 6. Based on this result, it is understood that the shifted peak position of the absorption spectrum of C—H bond appeared with the brominated flame retardant and the shifted peak position of the absorption spectrum of C—H bond appearing with the resin containing the brominated flame retardant substantially matches with each other. Further, measurements as to the other brominated flame retardants verified the similar phenomenon.

Thus, the inventors of the present invention has arrived at the idea that, by evaluating the shifted peak of each absorption spectrum of C—H bond shown in FIG. 6, a brominated flame retardant contained in resin can be detected.

In this case, a change in the peak of the absorption spectrum attributed to the effect of the brominated flame retardant is extremely small, as can also be seen from the result shown in FIG. 7. Further, near the peak of the absorption spectrum whose position has shifted under the effect of the brominated flame retardant, the peak of the absorption spectrum of the resin not containing the brominated flame retardant is present. That is, the inventors have derived from the experimental result shown in FIG. 6 that the following wavelength bands are desirable as the wavelength bands with which evaluation of the absorption spectrum is carried out in order to detect only the shifted peak.

The wavelength bands that are to be specifically evaluated are: the wavelength band of 1.42 μm or more and 1.44 μm or less; the wavelength band of 1.45 μm or more and 1.47 μm or less; the wavelength band of 1.66 μm or more and 1.68 μm or less; the wavelength band of 1.72 μm or more and 1.74 μm or less; the wavelength band of 1.92 μm or more and 1.94 μm or less; the wavelength band of 2.11 μm or more and 2.12 μm or less; the wavelength band of 2.17 μm or more and 2.20 μm or less; and the wavelength band of 2.31 μm or more and 2.34 μm or less. Evaluation of the absorption spectra as to these wavelength bands makes it possible to detect a brominated flame retardant by emission of near infrared light which cannot detect the inherent absorption spectrum of bromine, and to determine whether or not a brominated flame retardant is contained in resin.

The wavelength bands except for those noted above include absorption spectrum other than the shifted peak of absorption spectrum and, therefore, it is difficult to precisely detect and determine a brominated flame retardant contained in resin.

It is to be noted that, the method for detecting a brominated flame retardant using the brominated flame retardant determining apparatus 1 according to the first embodiment shown in FIG. 1A is intended to determine whether or not a brominated flame retardant is contained in the determination target object 2, and is not intended to specify the type of the brominated flame retardant. Therefore, focusing on the wavelength bands noted above, and when even a single shifted peak of the absorption spectrum attributed to a brominated flame retardant is detected in at least one of the wavelength bands, the determination target object 2 is determined to be the determination target object 2a that contains a brominated flame retardant. Irrespective of the type of the brominated flame retardant, the determination target object 2a determined to be containing a brominated flame retardant is stored in the disposal box 14. Accordingly, out of a plurality of determination target objects 2 which are unknown as to whether or not a brominated flame retardant is contained, only the determination target objects 2b determined to contain no brominated flame retardant can be selectively separated at high speeds.

Here, as the brominated flame retardant, a bromine compound is used. More specifically, the brominated flame retardant is one of PBB, PBDE, HBCDD, TBBPA, TBBPA-bis, and TBBPA derivatives.

It is to be noted that, in a case where the type of the brominated flame retardant to be detected can previously be specified, the wavelength band corresponding to that type of brominated flame retardant may be selected out of the wavelength bands noted above, and only the absorption spectrum in the selected wavelength band may be evaluated to thereby specify the type of the brominated flame retardant.

Next, a description will be given of a method of detecting a brominated flame retardant using the brominated flame retardant determining apparatus 1 whose description has been given with reference to FIGS. 1A to 5.

The arithmetic processing unit 10 determines whether or not a brominated flame retardant is contained, by evaluating the peak of the absorption spectrum of the determination target object 2 based on the output of the channels of the light receiving array 24. Specifically, detection of a brominated flame retardant is carried out by evaluating the absorption spectrum in: the wavelength band of 1.42 μm or more and 1.44 μm or less (3 and 4 channels); the wavelength band of 1.45 μm or more and 1.47 μm or less (6 and 7 channels); the wavelength band of 1.66 μm or more and 1.68 μm or less (27 and 28 channels); the wavelength band of 1.72 μm or more and 1.74 μm or less (33 and 34 channels); the wavelength band of 1.92 μm or more and 1.94 μm or less (53 and 54 channels); the wavelength band of 2.11 μm or more and 2.12 μm or less (72 channel); the wavelength band of 2.17 μm or more and 2.20 μm or less (78, 79, and 80 channels); and the wavelength band of 2.31 μm or more and 2.34 μm or less (92, 93, and 94 channels).

Further, the channels other than the channels used for detecting the brominated flame retardant are used for detecting the peak of the absorption spectrum of the resin itself. For example, it is known that the peak of the absorption spectrum of PP resin appears significantly around the wavelength of 1.75 μm. Therefore, the arithmetic processing unit 10 determines whether or not the determination target object 2 is PP resin or not, based on the output of 36 channel that can address the wavelength around 1.75 μm.

It is to be noted that, since the peak of the absorption spectrum of PP resin appears more clearly than the peak of the brominated flame retardant, an extremely high resolution is not required. Therefore, the channels other than those used for determining a brominated flame retardant, for example, the optical fibers 25 corresponding to 10 channel, 11 channel, and 12 channel may be connected to the identical light receiving element 30 via the connector 29. In this case, the wavelength band falling within a range of from 1.49 μm or more to 1.52 μm or less is detected with the resolution of 0.03 μm. The channel used for determining a brominated flame retardant is detected with 0.01 μm. In this manner, by appropriately selecting the resolution, the number of plotting of the absorption spectrum can be minimized. This can avoid excessive processing more than necessary and can further shorten the processing time and, therefore, it becomes possible to further reduce the detection time.

Further, when there is any channel that corresponds to the wavelength band not used for evaluation (for example, when the wavelength entering 110 channel is not used for evaluation in determining any types of resin), the optical fiber 25 corresponding to 110 channel may not be connected to the light receiving element 30. A reduction in the wavelength bands of the absorption spectrum used for evaluation can shorten the processing time, and time required for determination can further be reduced.

Further, it may be possible to increase the number of the optical fibers 25 for increasing the resolution. However, an increase in the number of the optical fibers 25 reduces the light quantity entering each optical fiber 25. An increase in the light quantity of light sources such as the halogen lamps 5 is limited order to supplement lack of the light quantity, it is necessary to reduce the speed of conveying the determination target objects 2, which disadvantageously increases the time until determination.

Accordingly, the first embodiment employs the light receiving array 24 having 110 pieces of optical fibers 25 as the light receiving unit that can fully detect a brominated flame retardant without reducing the speed of conveying the determination target objects.

Figure 1B:
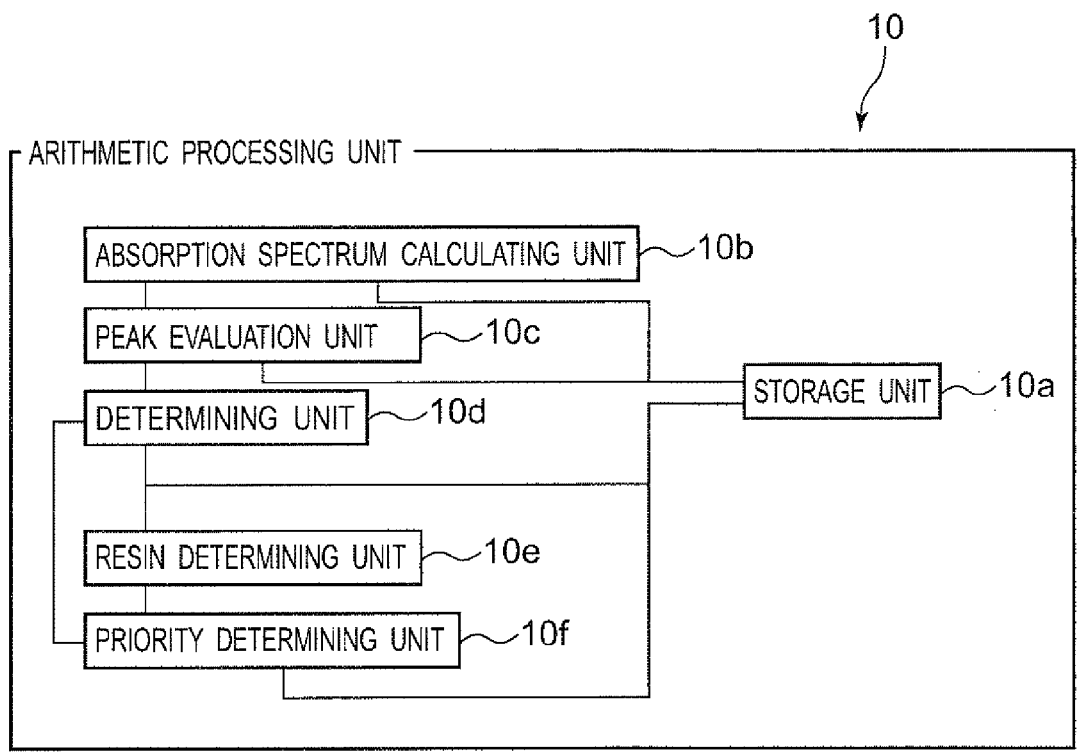
FIG. 1B is a block diagram of an arithmetic processing unit of the brominated flame retardant determining apparatus according to the first embodiment of the present invention.

With the arithmetic processing unit 10, data matching is carried out based on previously stored data about the absorption spectrum of resin and a brominated flame retardant, to determine the type of resin of the determination target object 2 and whether or not a brominated flame retardant is contained. More specifically, as shown in FIG. 1B, the arithmetic processing unit 10 includes: a storage unit 10*a* that stores data of the absorption spectra of resin and a brominated flame retardant; an absorption spectrum calculating unit 10*b* that calculates the absorption spectrum of the determination target object 2 from the information of reflected light 9 detected by the light receiving array 24 of the near infrared light detecting device 6 based on the information in the storage unit 10*a*; a peak evaluation unit 10*c* that evaluates the shifted peak based on the calculation result by the absorption spectrum calculating unit 10*b*; and a determining unit 10*d* that determines whether or not a brominated flame retardant is contained the determination target object 2 based on the evaluation by the peak evaluation unit 10*c*. Information required for evaluation by the peak evaluation unit 10*c* (wavelength bands to be used in evaluation and the like) and determination result by the determining unit 10*d* and the like are also stored in the storage unit 10*a*. The arithmetic processing unit 10 may further include a resin determining unit 10*e* that determines the type of resin of the determination target object 2, and a priority determining unit 10*f* that determines priority of the wavelength bands based on the determination result by the resin determining unit 10*e*, so that the determining unit 10*d* determines whether or not a brominated flame retardant is contained in the determination target object 2 based on the absorption spectrum in the wavelength band based on the priority determined by the priority determining unit 10*f*. The determination result by the resin determining unit 10*e*, the determination result by the determining unit 10*d* and the like are also stored in the storage unit 10*a*.

What is required as a determination algorithm herein is a method of extracting required information from multivariate characteristics amounts of the absorption spectrum of near infrared light. Therefore, generally, a determination method based on the muitivariate analysis by the chemometrics method is effective. The chemometrics method is a method for estimating the effective result by an optimum processing method using a mathematical scheme or a statistical scheme from obtained numerous and multivariant data.

Other determination algorithm is the linear multiple regression analysis method or the principal component analysis method. The PLS (Partial Least Squares) regression analysis method is also effective. Further, the cluster analysis is appropriate, in which a determination using Mahalanobis distance or asymmetric Mahalanobis distance is effective. However, which algorithm is to be employed is selected properly.

Is considered a case of evaluating spectra with, out of the detected wavelength bands: the wavelength band of 1.42 μm or more and 1.44 μm or less; the wavelength band of 1.45 μm or more and 1.47 μm or less; the wavelength band of 1.66 μm or more and 1.68 μm or less; the wavelength band of 1.72 μm or more and 1.74 μm or less; the wavelength band of 1.92 μm or more and 1.94 μm or less; the wavelength band of 2.11 μm or more and 2.12 μm or less; the wavelength band of 2.17 μm or more and 2.20 μm or less; and the wavelength band of 2.31 μm or more and 2.34 μm or less. In this case, when comparison against a preset threshold value shows that the detected spectrum value exceeds the threshold value, it may be determined that a brominated flame retardant is contained. Conversely, when the detected spectrum value does not exceed the threshold value, it is determined that a brominated flame retardant is not contained.

Further, since the wavelength bands noted above are each a wavelength band in which the peak of the absorption spectrum of C—H bond contained in resin is at a position shifted from the inherent position, in a wavelength band adjacent to each wavelength band noted above, the absorption spectrum is varied as being attributed to the shift of the peak position of the absorption spectrum, as compared to the resin in a state containing no brominated flame retardant. Hence, as to the wavelength band adjacent to each wavelength band noted above also, a brominated flame retardant can be detected more precisely by evaluating the absorption spectrum.

Figure 8:
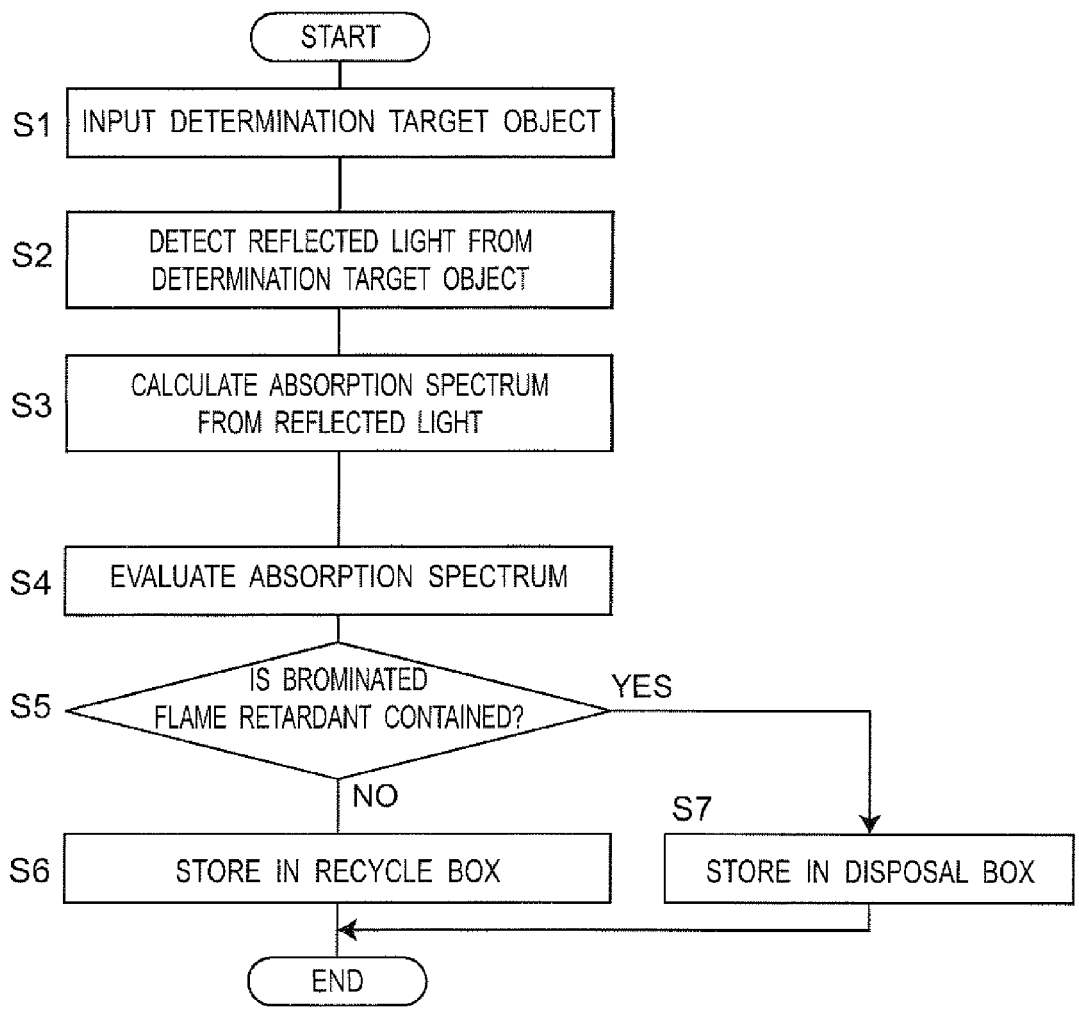
FIG. 8 is a flowchart showing a flow of the brominated flame retardant determining apparatus according to the first embodiment of the present invention selectively separating determination target objects.

Next, with reference to FIG. 1B and based on the flowchart of FIG. 8, a description will be given of an operation of the brominated flame retardant determining apparatus 1 shown in FIG. 1.

Here, focusing on a single determination target object 2 out of a plurality of pieces of resin, a description will be given of its flow until being selectively separated.

First, in Step S1, the determination target object 2 placed on the hopper 4 is inputted to an arbitrary place in the input region 3A on the conveyer belt 3 that shifts at a constant speed by the vibration or rocking operation of the hopper 4.

Next, in Step S2, the near infrared light detecting device 6 (the light receiving array 24 shown in FIG. 4) detects the reflected light 9 dispersed for each wavelength band from the determination target object 2 that has arrived at the detection region 35.

Next, in Step S3, information of the reflected light 9 detected by the near infrared light detecting device 6 is outputted from the near infrared light detecting device 6 to the arithmetic processing unit 10. The arithmetic processing unit 10 calculates the absorption spectrum of the determination target object 2 by the absorption spectrum calculating unit 10*b*, based on the inputted information of reflected light 9.

Next, in Step S4, from the absorption spectrum calculated by the absorption spectrum calculating unit 10*b*, whether or not the value of the peak shifted into the range of wavelength bands noted above is compared against the preset threshold value, to determine whether or not the shifted peak value exceeds the threshold value by the peak evaluation unit 10*c*.

Next, in Step S5, based on the evaluation made by the peak evaluation unit 10*c* of the arithmetic processing unit 10, whether or not a brominated flame retardant is contained in the determination target object 2 is determined by the determining unit 10*d*. Specifically, when it is evaluated that the shifted peak value exceeds the threshold value by the peak evaluation unit 10*c*, the determining unit 10*d* determines that a brominated flame retardant is contained. When the peak evaluation unit 10*c* evaluates that the shifted peak value does not exceed the threshold value, the determining unit 10*d* determines that no brominated flame retardant is contained.

Next, when the determining unit 10*d* determines that no brominated flame retardant is contained (NO in Step S5), the operation flow proceeds to Step S6. In Step S6, the pulse air nozzle 12 blows air to the determination target object 2*b* determined to be containing no brominated flame retardant by the determining unit 10*d* while freely falling from the terminal portion 11 of the conveyer belt 3. Thus, the determination target object 2*b* determined to be containing no brominated flame retardant is stored in the recycle box 13.

On the other hand, when it is determined to be containing a brominated flame retardant (YES in Step S5), the operation flow proceeds to Step S7. In Step S7, the pulse air nozzle 12 does not blow air to the determination target object 2a determined to be containing a brominated flame retardant, and the determination target object 2a freely falls from the terminal portion 11 of the conveyer belt 3 and is stored in the disposal box 14.

As described in the foregoing, according to the brominated flame retardant determining method according to the first embodiment, whether or not a brominated flame retardant is contained in the determination target object 2 can be determined by the arithmetic processing unit 10 at high speeds. Thus, out of a plurality of determination target objects 2 which are unknown as to whether or not a brominated flame retardant is included, only the determination target objects 2b determined to be containing no brominated flame retardant can selectively be separated at high speeds.

Further, being different from the conventional method using FT-IR, the brominated flame retardant determining method does not require preprocessing. Hence, the required time for preprocessing (approximately 10 minutes) per determination target object 2 can be dispensed with for every determination target object 2. That is, the measurement time can be reduced by: the number of pieces of the determination target objects 2× the preprocessing time. Further, in contrast to the FT-IR which requires time of, e.g., approximately 1.6 seconds, from emission of mid infrared light until determination, the brominated flame retardant determining method according to the first embodiment can achieve determination by, e.g., approximately 1 millisecond (1/1000 seconds), from emission of near infrared light.

It is to be noted that, as a specific example, in connection with the brominated flame retardant determining apparatus 1 shown in FIG. 1A, the width of the conveyer belt 3 is 1 m, and the length from the hopper 4 to the position of the terminal portion 11 on the conveyer belt 3 is 10 m. The width of the conveyer belt 3 can arbitrarily be determined by the required processing performance and the installation cost. Further, as to the length of the conveyer belt 3 also, the distance with which the motion caused by the determination target object 2 being inputted by the hopper 4 converges and the position of the determination target object 2 on the conveyer belt 3 stabilizes will suffice.

Further, as one example, the determination target object 2 is a small piece of resin each side of which is from approximately some tens mm or less to 5 mm or more. This dimension is determined by the size of the determination target object 2 actually conveyed on the conveyer belt 3 and the spatial resolution of the near infrared light detecting device 6. Determination target object 2 which is too small for the determination is previously selectively separated so as not to be mixed with. In the first embodiment, one exemplary dimension of the determination target object 2 previously selectively separated is the determination target object 2 having each side measuring 5 mm or less.

Further, the conveying speed of the conveyer belt is selected by the required amount of selective separation. As one example, 1 m/s or more and 5 m/s or less is preferable. In the first embodiment, the conveying speed is 3 m/s.

It is to be noted that, as one example of an emission unit, the halogen lamps 5 each having a broad wavelength band of 1.40 μm or more and 2.50 μm or less as the emitted wavelength are used. However, laser or LED light sources having a wide wavelength band may be used. As to the emitted wavelength bands, the wavelength bands with which a peak of an absorption spectrum required to determine a brominated flame retardant or resin to be detected can occur will suffice.

As one example, the blaze wavelength of the diffraction grating 22 is 2.0 μm, and the grating pitch is 200 pieces/mm. In this manner, a dispersion angle of approximately 12 degrees can be obtained in the band of 1.40 μm or more and 2.50 μm or less can be obtained. It is to be noted that, when there is a wavelength band which is particularly desired to be detected, the blaze wavelength of the diffraction grating 22 can be selected from a range of from 1.40 μm or more to 2.50 μm or less. The grating pitch may also be selected from a range of 100 pieces/mm or more and 300 pieces/mm or less.

It is to be noted that, as one example, the angle of the diffraction grating 22 to the optical axis 15 shown in FIG. 4 is preferably 5 degrees to 40 degrees, though it depends on the second order reflected light from the diffraction grating 22.

It is to be noted that, when condensing light by the condenser lens 23 on the optical fibers 25, optical aberration causes the condense spot to be approximately 50 μm or more and 100 μm or less, as one example. Accordingly, in order to secure sufficient light quantity and to improve the detection speed, the desirable core diameter is not of several μm which is generally employed for optical fibers, but the desirable core diameter is the core diameter of approximately 100 μm or more and 1000 μm or less as one example.

It is to be noted that, as one example, in a case where the cladding diameter is great relative to the core diameter, e.g., the cladding diameter is 1000 μm while the core diameter is 500 μm, the cladding layer is present at a thickness of 250 μm around the core, and even when the optical fibers 25 are aligned as being brought into contact with one another, there exists a band in which light cannot be collected by the layer of 250 μm. In this case, the wavelengths of the light cannot continuously be collected, and the bands have a missing value. Therefore, it is desirable that the condition in which the core diameter and the cladding diameter are substantially equivalent. Desirably, the ratio between the core diameter and the cladding diameter is 1:1 or more and 1:1.2 or less, for example.

It is to be noted that, though the light receiving array 24 has been shown as an example of the light receiving unit, it is not limited thereto. The light receiving unit may be structured with a plurality of image sensors, e.g., avalanche photodiode (APD) elements.

It is to be noted that, since the light receiving elements 30 differ from one another in conversion efficiency depending on the wavelength bands, efficient elements from the short wavelength side to the long wavelength side of incidental light may respectively be selected.

It is to be noted that, since the light of 2.50 μm or more (mid infrared light) has great transmission loss in a normal optical system and is naturally filtered, the wavelength filter 16 that cuts off the light of, e.g., 1.40 μm or less, may be employed.

It is to be noted that, it may be also possible to allow light of an arbitrary wavelength band to enter the near infrared Eight detecting unit 8 by a combination of the halogen lamps 5 and the wavelength filter 16. For example, when it is to determine only whether or not a brominated flame retardant is contained, the light whose wavelength band spans from 1.42 μm to 2.34 μm solely may be allowed to enter the near infrared light detecting unit 8.

It is to be noted that, brominated flame retardants differ from one another in compatibility or the flame-retardant effect depending on the type of resin. Accordingly, a flame retardant that is used can be specified by the type of resin. Generally, a flame retardant used for ABS resin is TBBPA or a TBBPA derivative.

Figure 12:
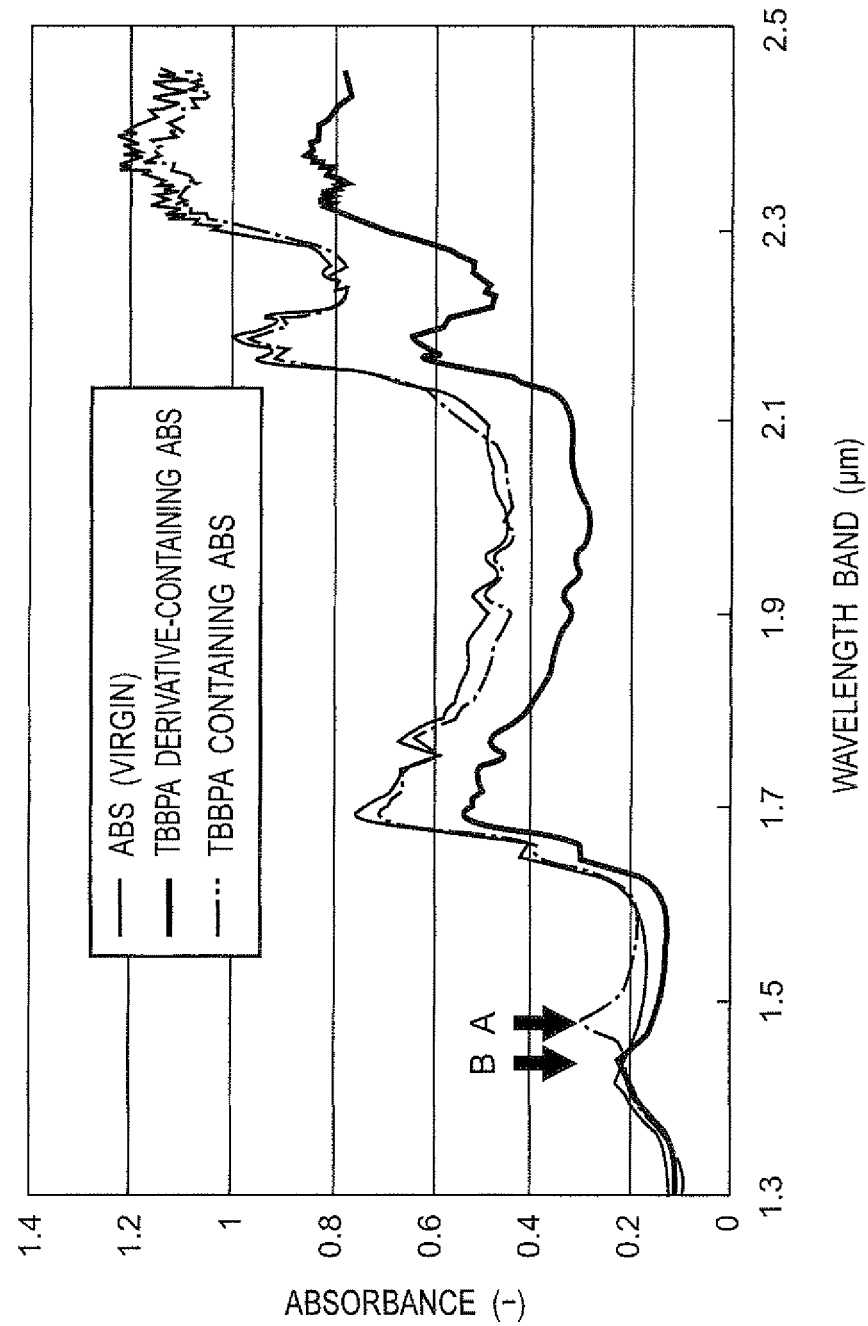
FIG. 12 is a graph showing the absorption spectra used for determining whether or not a brominated flame retardant is contained in ABS resin with a recycled material selectively separating apparatus according to a variation of the first embodiment of the present invention.

Here, FIG. 12 is a graph showing the comparison of absorption spectra among virgin ABS resin to which no brominated flame retardant is added, ABS resin to which a TBBPA flame retardant is added, and a TBBPA derivative flame retardant is added (bromine concentration 15% (mass fraction), flame retardant grade V0). In the graph of FIG. 12, the horizontal axis indicates wavelength and the vertical axis indicates absorbance. Since the ABS resin that contains TBBPA has a difference at the wavelength band of 1.45 µm or more and 1.47 µm or less (the position indicated by arrow A in the figure) between the virgin ABS resin, by setting the wavelength band to be used in evaluating the absorption spectrum to 1.45 µm or more and 1.47 µm or less, the arithmetic processing unit 10 can selectively separate them from one another.

Based on the similar idea, in a case where the ABS resin containing TBBPA derivative and the virgin ABS resin are to selectively be separated from each other, by using the absorption spectrum at the wavelength band of 1.42 µm or more and 1.44 µm or less (the position indicated by arrow B in the drawing) for the evaluation by the arithmetic processing unit 10, they can selectively be separated from each other.

That is, when the determination target object 2 is composed of ABS resin as a variation, based on the absorption spectrum of the wavelength band of at least one of the wavelength band of 1.42 µm or more and 1.44 µm or less, and the wavelength band of 1.45 µm or more and 1.47 µm or less, the arithmetic processing unit 10 determines whether or not a brominated flame retardant is contained in the determination target object 2. Thus, in a case where the determination target object 2 is composed of ABS resin, whether or not a brominated flame retardant is contained in this determination target object 2 can be determined with high precision.

Second Embodiment

Next, a description will be given of a recycled material selectively separating apparatus 33 using the method of determining a brominated flame retardant according to the first embodiment. The recycled material selectively separating apparatus 33 according to a second embodiment is an apparatus that selectively separates and collects a recycled material being a particular resin that contains no brominated flame retardant from a plurality of determination target objects 2 each of which is unknown as to whether or not a brominated flame retardant is contained.

In the following, the structures identical to those in the first embodiment are denoted by the identical reference characters, and a description thereof will not be repeated. Further, since the structure of the arithmetic processing unit 10 shown in FIG. 1B is common to the first embodiment and the second embodiment, the structure shown in FIG. 1B is also used in the second embodiment.

Figure 9:
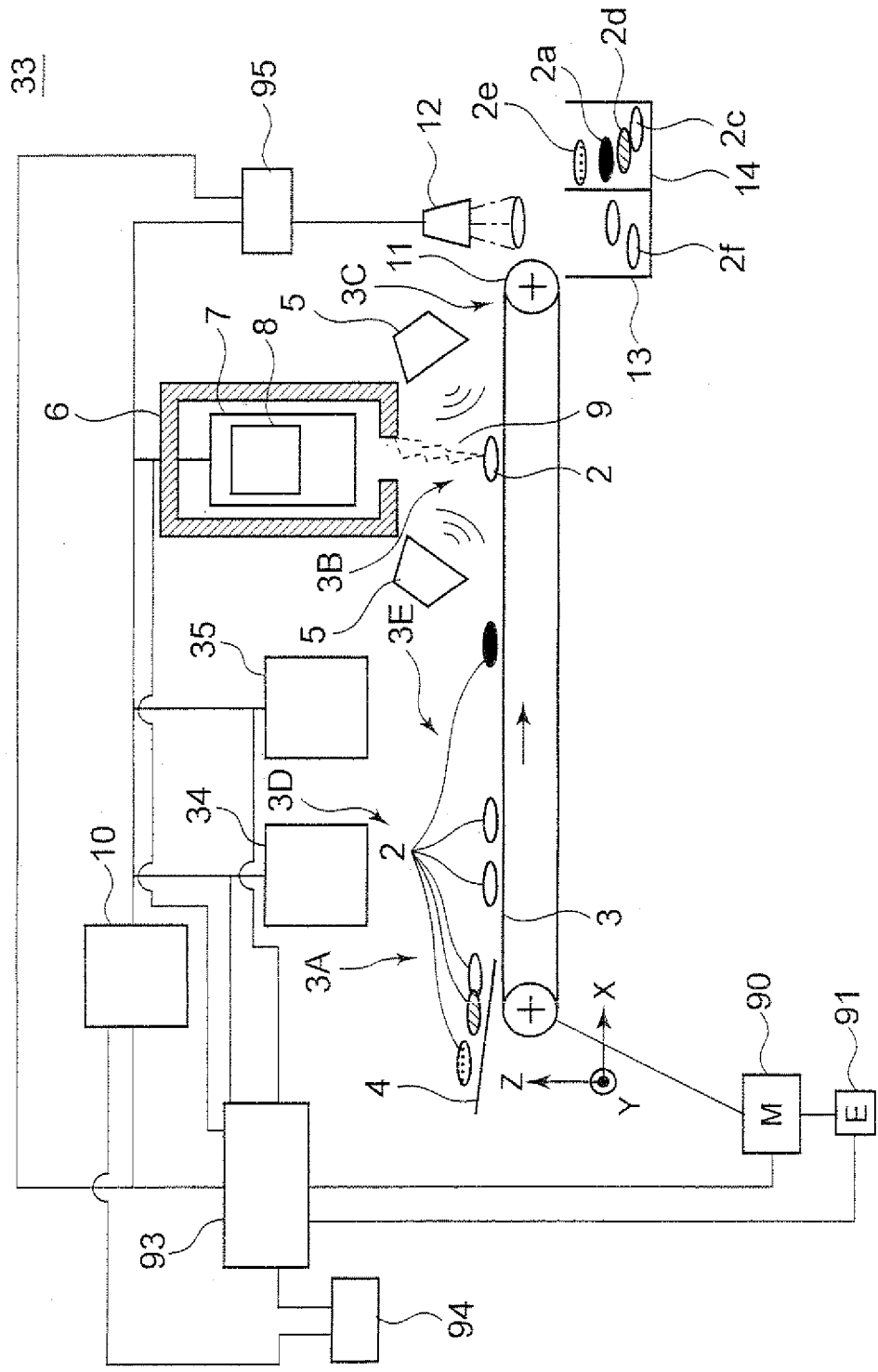
FIG. 9 is a schematic view of a recycled material selectively separating apparatus according to a second embodiment of the present invention.

With reference to FIGS. 9 and 1B, a description will be given of the recycled material selectively separating apparatus 33. The recycled material selectively separating apparatus 33 is different from the brominated flame retardant determining apparatus 1 according to the first embodiment in including a metal sensor 34 and a high-speed linear CCD camera 35, which are respectively arranged above a metal detection region 3D and a black color detection region 3E between the input region 3A and the detection region 3B of the conveyer belt 3. The metal sensor 34 is such a sensor that point-by-point detecting magnetic sensors are aligned in line in the conveying direction of the conveyer belt 3. The metal sensor 34 detects metal attached to the determination target object 2, or metal that is present in the surroundings of the determination target object 2. The determination target object 2c that is determined that metal is detected on itself and in its surroundings by the metal sensor 34 in the metal detection region 3D reaches the selectively separating region 3C, and thereafter is stored in the disposal box 14. This is to prevent metal from being mixed with the determination target object 2f determined to be a recycled material in the recycle box 13. The determination target object 2 with which no metal is detected including its surroundings is selectively separated by the selectively separation method according to the first embodiment.

The high-speed linear CCD camera 35 is an imaging sensor for imaging the determination target object 2. In a case where the determination target object 2 is nearly black in color, most of infrared light is absorbed, and the infrared light reflected from the determination target object 2 cannot be detected. Hence, the near infrared light detecting device 6 cannot recognize the determination target object 2. Accordingly, in order to detect a nearly black determination target object 2, the high-speed linear CCD camera 35 is installed. In a case where the near infrared light detecting device 6 does not recognize but the high-speed linear CCD camera 35 solely detects the determination target object 2, the determining unit 10d of the arithmetic processing unit 10 determines the determination target object 2 to be a determination target object 2d whose material is unknown. This determination target object 2d is stored in the disposal box 14.

The information of the metal sensor 34 and that of the high-speed linear CCD camera 35 are inputted to the arithmetic processing unit 10.

In order to integrate the information from each of the sensors 34 and 35, it is necessary to precisely obtain the position of the determination target object 2. As to the positional information, by acquiring the value of the encoder detector 91 of the motor 90 of the conveyer belt 3 whose operation is controlled by the control unit 93, and the arrangement positions of each of the near infrared light detecting device 6, the metal sensor 34, and the high-speed linear CCD camera 35, the position of the determination target object 2 on the conveyer belt 3 can be specified.

In this case, only when none of the determination target object 2d whose material is unknown and metal is not present including the surroundings of the determination target object 2f determined to be the recycled material, air is blown by the pulse air nozzle 12 to the determination target object 2f. This is to prevent the determination target object 2d or metal from being mixed in the recycle box 13.

Figure 10A:
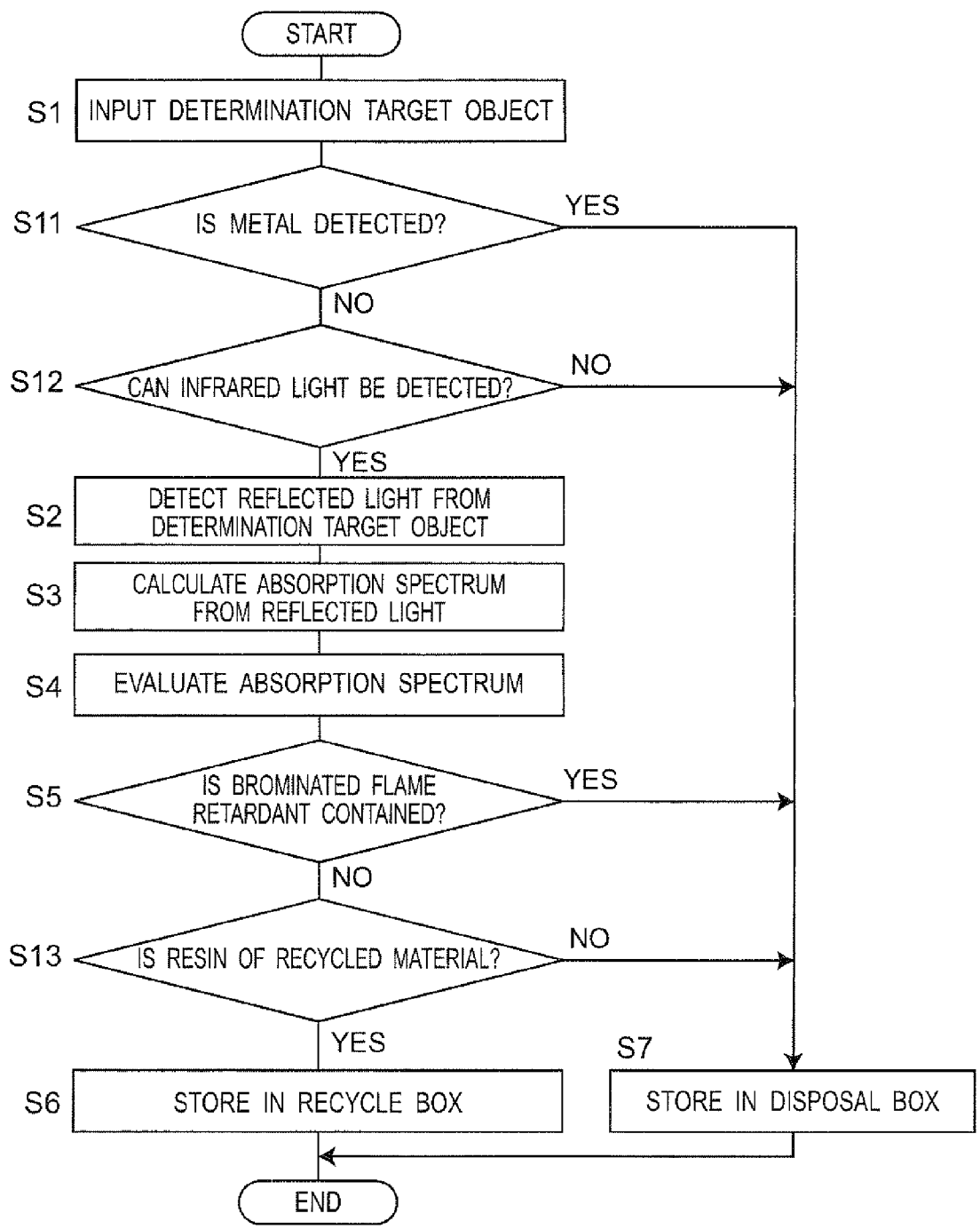
FIG. 10A is a flowchart showing a flow of the recycled material selectively separating apparatus according to the second embodiment of the present invention selectively separating determination target objects.

Next, with reference to FIGS. 9 and 1B and according to the flowchart of FIG. 10A, a description will be given of a flow of selectively separating the recycled materials by the recycled material selectively separating apparatus 33 according to the second embodiment. Here, PP resin is selected as the resin to be stored in the recycle box 13 as the recycled material.

First, in Step S1, the determination target object 2 placed on the hopper 4 is inputted to an arbitrary place in the input region 3A on the conveyer belt 3 that moves at a constant speed by the vibration or rocking operation of the hopper 4.

Next, in Step S11, the metal sensor 34 performs a metal inspection of the determination target object 2 at the metal detection region 3D. In connection with the determination target object 2 having passed through the metal detection region 3D, the determining unit 10d determines as to whether or not metal is attached to the determination target object 2 or metal is present in the surroundings of the determination target object 2, based on the information from the metal sensor 34. When the metal attached to the determination target object 2 or metal in the surroundings of the determination target object 2 is detected (YES in Step S11), the operation flow goes to Step S7. In Step S7, when the determination target object 2c arrives at the selectively separating region 3C of the conveyer belt 3, the determination target object 2c freely falls from the terminal portion 11 of the conveyer belt 3 of the selectively separating region 3C, and is stored in the disposal box 14. In Step S11, when metal attached to the determination target object 2 or metal in the surroundings of the determination target object 2 is not detected (NO in Step S11), the operation flow proceeds to Step S12.

In Step S12, the high-speed linear COD camera 35 performs imaging of the determination target object 2 at the black color detection region 3E. The determining unit 10*d* determines whether or not infrared light reflected from the determination target object 2 can be detected based on the imaging information of the high-speed linear COD camera 35 and the recognition information at the detection region 3B of the near infrared light detecting device 6. When the determination of the determining unit 10*d* shows that the determination target object 2 is nearly black and near infrared light cannot be detected, and hence the determination target object 2 is determined to be the determination target object 2*d* whose material is unknown (NO in Step S12), the process proceeds to Step S7. In Step S7, when the determination target object 2*d* whose material is unknown arrives at the selectively separating region 3C of the conveyer belt 3, the determination target object 2*d* freely fails from the terminal portion 11 of the conveyer belt 3 of the selectively separating region 3C, and is stored in the disposal box 14. When the determination target object 2 is not black and is determined to be the determination target object 2*d* with which near infrared light can be detected based on the determination at the determining unit 10*d* (YES in Step S12), the operation flow proceeds to Step S2.

In Step S2, the near infrared light detecting device 6 detects the reflected light 9 being dispersed for each wavelength band from the determination target object 2 having been inputted and has arrived at the detection region 3B.

Next, in Step S3, the information of the reflected light 9 detected by the near infrared light detecting device 6 is outputted from the near infrared light detecting device 6 to the arithmetic processing unit 10, and from the information of the reflected light 9 being inputted to the arithmetic processing unit 10, the absorption spectrum of the determination target object 2 is calculated by the absorption spectrum calculating unit 10*b*.

Next, in Step S4, based on the absorption spectrum calculated by the absorption spectrum calculating unit 10*b*, the peak evaluation unit 10*c* compares the peak value shifted in the wavelength range described in the first embodiment against a preset threshold value, to evaluate whether or not the shifted peak value exceeds the threshold value.

Next, in Step S5, based on the evaluation by the peak evaluation unit 10*c* of the arithmetic processing unit 10, the determining unit 10*d* determines whether or not a brominated flame retardant is contained in the determination target object 2. Specifically, when the peak evaluation unit 10*c* evaluates that the shifted peak value exceeds the threshold value, the determining unit 10*d* determines that a brominated flame retardant is included. When the peak evaluation unit 10*c* evaluates that the shifted peak value does not exceed the threshold value, the determining unit 10*d* determines that a brominated flame retardant is not contained.

When the determining unit 10*d* determines that a brominated flame retardant is contained (YES in Step S5), the operation flow proceeds to Step S7. In Step S7, to the determination target object 2*a* determined to be containing a brominated flame retardant, air is not blown by the pulse air nozzle 12, and the determination target object 2*a* freely falls from the terminal portion 11 of the conveyer belt 3, and is stored in the disposal box 14.

On the other hand, when the determining unit 10*d* determines that no brominated flame retardant is contained (NO in Step S5), the operation flow proceeds to Step S13. In Step S13, the resin determining unit 10*e* of the arithmetic processing unit 10 determines the type of resin of the determination target object 2 based on the information from the near infrared light detecting device 6. When the resin determining unit 10*e* determines that the type of resin of the determination target object 2 is not PP resin being the recycled material (NO in Step S13), the operation flow proceeds to Step S7. In Step S7, the determination target object 2*e* freely falls from the terminal portion 11 of the conveyer belt 3, and is stored in the disposal box 14. On the other hand, when the resin determining unit 10*e* determines that the type of resin of the determination target object 2 is PP resin being the recycled material (YES in Step S13), the operation flow proceeds to Step S6. In Step S6, while the determination target object 2*f* is freely falling from the terminal portion 11 of the conveyer belt 3, the air supply source 95 is driven under control of the control unit 93 based on the determination result of the resin determining unit 10*e*, and air is blown by the pulse air nozzle 12. Thus, the determination target object 2*f* being PP resin containing no brominated flame retardant is stored in the recycle box 13 as the recycled material.

In the manner described above, the determination target objects 2 are selectively separated using the recycled material selectively separating apparatus 33. Thus, the resin containing no impurities such as brominated flame retardants or metal can quickly be collected. Accordingly, the collected resin can be applied as a recycled material of high quality. Further, since the near infrared light is used for determining the determination target object 2, the apparatus can be manufactured at further lower costs than a conventional apparatus using mid infrared light. When an apparatus of a low cost is realized, recycling of resin becomes more popular, and the environmental burden can be reduced.

It is to be noted that, it is also possible to realize the recycled material selectively separating apparatus 33 and the recycled material selectively separating method as a recycling apparatus and a recycling method by reusing the determination target object 2*f* which is determined to be containing no brominated flame retardant as the recycled material and thereafter selectively separated by the selectively separating unit 12. As a reusing method, the method disclosed in Japanese Unexamined Patent Publication No. 2001-205632 can be employed. In this case, in order to reuse the determination target object 2*b* (or 2*f*) determined to be containing no brominated flame retardant, the selectively separating unit 12 has a function of selectively separating the determination target object 2*a* determined to be containing a brominated flame retardant and a determination target object 2*b* (or 2*f*) determined to be containing no brominated flame retardant from each other.

It is to be noted that, the positional relationship of the near infrared light detecting device 6, the metal sensor 34, and the high-speed linear CCD camera 35 can be rearranged not being limited to the mode of the second embodiment.

Further, it is also possible to allow the arithmetic processing unit 10 to compositely determine information from the near infrared light detecting device 6, information from the metal sensor 34, and information from the high-speed linear CCD camera 35, to determine whether the determination target object 2 is to be stored in the recycle box 13 or in the disposal box 14.

It is to be noted that, though the distance determined to be the surroundings of the determination target object 2 as used herein can arbitrarily be set, the distance depends on the spatial resolution of air-blow at the final selective separation step.

Subsequently, as one variation, a description will be given of operations including: determining the type of resin of the determination target object 2; evaluating the peak in the wavelength band corresponding to the determined resin; and determining whether or not a brominated flame retardant is contained in the determination target object 2. Here, as the type of resin, PP resin, ABS resin, and PS (polystyrene) resin are exemplarily shown. Further, FIG. 10B shows the flow of the operation in this variation, and a description will be given of FIG. 10B as to its operation being different from FIG. 10A.

Figure 10B:
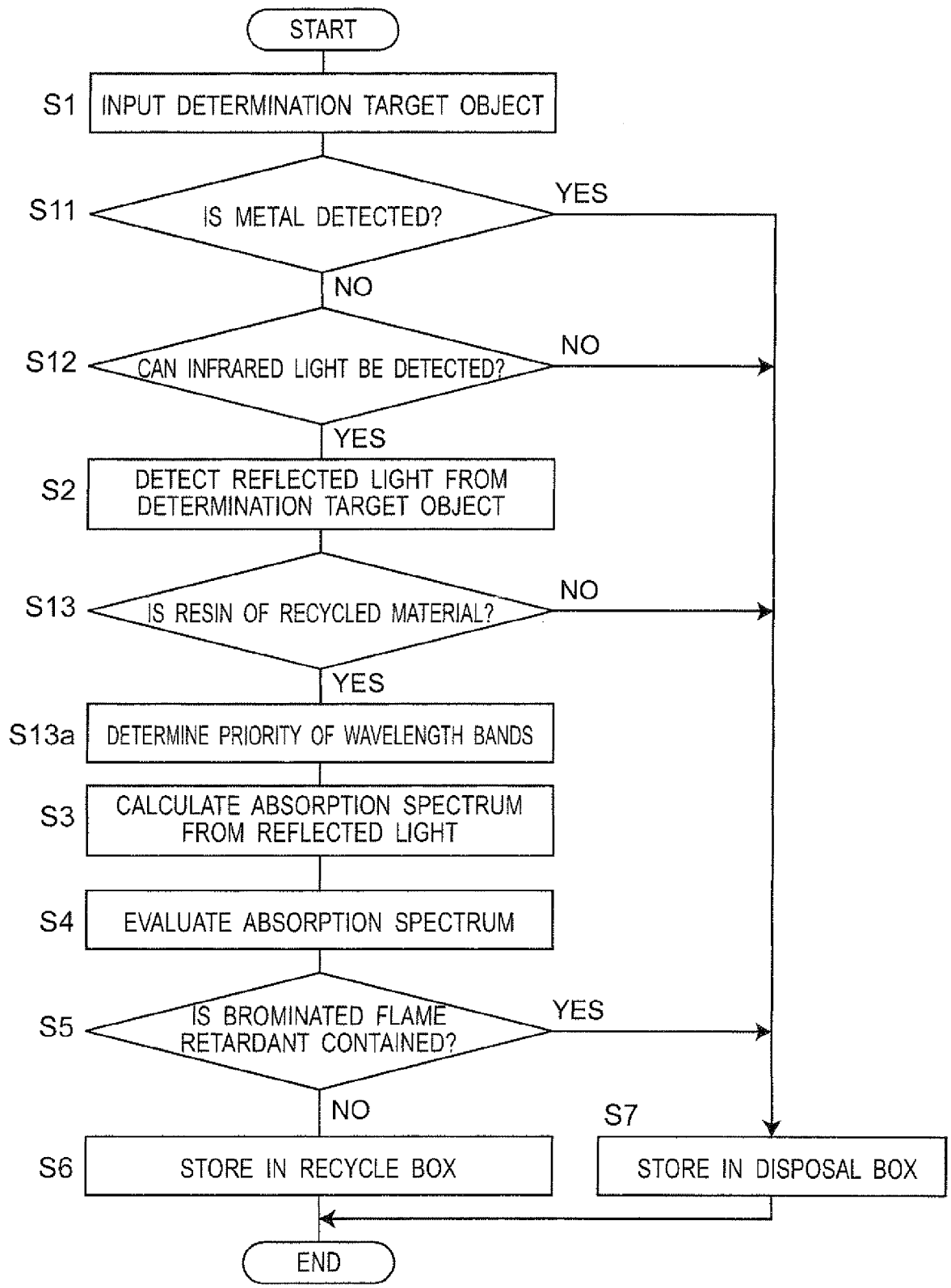
FIG. 10B is a flowchart showing a flow of a recycled material selectively separating apparatus according to a variation of the second embodiment of the present invention separately selecting determination target objects.
Figure 11:
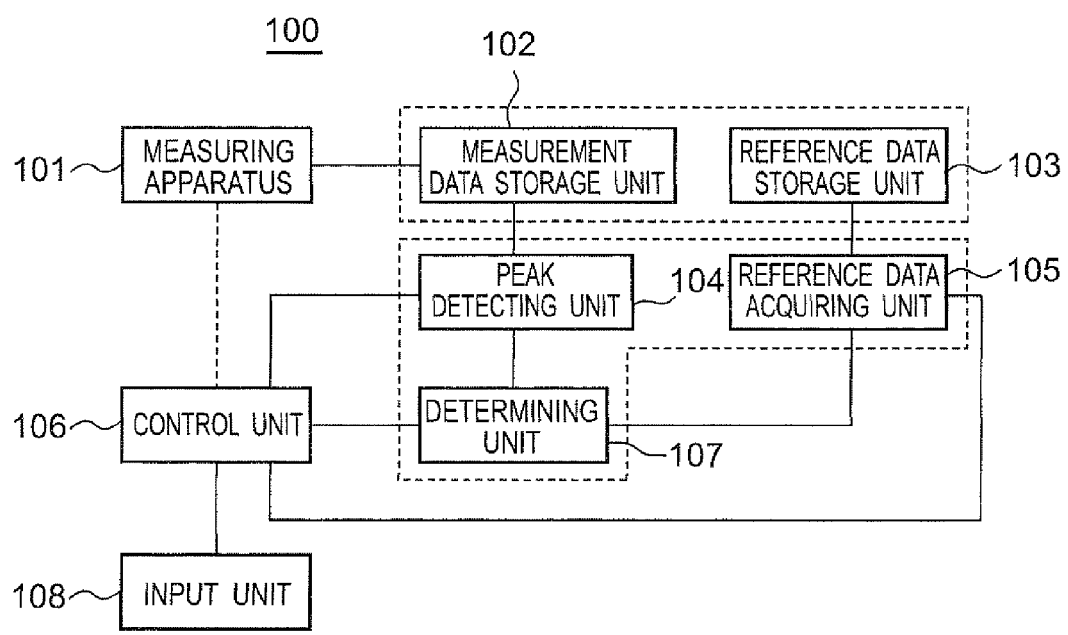
FIG. 11 is a schematic view showing the schematic structure of a conventional brominated flame retardant determining apparatus using the conventional FT-IR.

As shown in FIG. 10B, after Step S2, in Step S13, the resin determining unit 10e of the arithmetic processing unit 10 determines the type of resin of the determination target object 2. It is known that: PP resin has a peak in the wavelength band around 1.75 μm because PP resin has $CH_3$ methyl group; each of ABS resin and PS resin each having CH aromatic has a peak in the wavelength band around 1.69 μm; and ABS resin has a peak in the wavelength band around 1.96 μm attributed to the molecular structure contained in acrylonitrile. The type of resin can be determined by detecting the peaks by the near infrared detecting device.

Next, based on the determination result of the type of resin determined by the resin determining unit 10e, the priority determining unit 10f determines the priorities of the wavelength bands used in determining at Step S5 (Step S13a). In some cases, the detection process of a brominated flame retardant related to particular wavelength bands is not necessary depending on the type of resin in terms of manufacture. In order to eliminate such unnecessary wavelength bands, the priority determination of the wavelength bands is performed. As one example, when the determination target object 2 is ABS resin, the first and second priorities are the wavelength band of 1.42 μm or more and 1.44 μm or less, and the wavelength band of 1.45 μm or more and 1.47 μm or less, respectively, and the unnecessary wavelength bands (the wavelength bands of lower priorities) are: the wavelength band of 1.66 μm or more and 1.68 μm or less; the wavelength band of 1.72 μm or more and 1.74 μm or less; the wavelength band of 1.92 μm or more and 1.94 μm or less; the wavelength band of 2.11 μm or more and 2.12 μm or less; the wavelength band of 2.17 μm or more and 2.20 μm or less; and the wavelength band of 2.31 μm or more and 2.34 μm or less. Information on those wavelength bands of higher priorities and the wavelength bands of lower priorities are previously stored in the storage unit 10a connected to the priority determining unit 10f, in association with the types of resin. Thus, based on the type of resin of the determination target object 2 determined by the resin determining unit 10e in Step S13, the brominated flame retardant detection work (the absorption spectrum calculating process) can be performed using only the wavelength bands of higher priorities, and hence the processing can more efficiently be performed.

Next, whether or not a brominated flame retardant is contained in the determination target object 2 is determined based on the absorption spectrum in the wavelength bands based on the priorities determined by the priority determining unit 10f. That is, in Step S3, it is also possible for the absorption spectrum calculating unit 10b to calculate the absorption spectrum in the wavelength bands of higher priorities depending on the resin. Thereafter, similarly to the manner shown in FIG. 10A, the operations from Steps S4 to S6 or S7 are performed by the absorption spectrum calculating unit 10b, the peak evaluation unit 10c, and the determining unit 10d. It is to be noted that, in Step S4, the absorption spectrum in the wavelength bands of higher priorities may be evaluated by the peak evaluation unit 10c of the arithmetic processing unit 10 depending on the resin.

As in the variation, by using only the wavelength bands of higher priorities for determination, the efficiency of the processing can be improved. Further, though the information from the wavelength bands not required for determination of a brominated flame retardant may affect the determination result as noises, by using only the wavelength bands of higher priority for determination, the effect of such noises can be suppressed.

It is to be noted that, by combining any of the foregoing various embodiments or variations as appropriate, their respective effects can be exhibited. For example, the operations of the Steps S13 and S13a shown in FIG. 10B described in the variation may be performed between Step S2 and Step S3 in the flow of FIG. 8 of the first embodiment.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

INDUSTRIAL APPLICABILITY

The brominated flame retardant determining method, the brominated flame retardant determining apparatus, the recycling method, and the recycling apparatus of the present invention can quickly determine whether or not a brominated flame retardant is contained in a mixture of a plurality of types of resin based on the foregoing. Therefore, they can be applied to, e.g., recycling steps for quickly and selectively separating a plurality of selective separation target objects.

The invention claimed is:

1. A brominated flame retardant determining method, comprising:
   emitting light to a determination target object composed of resin;
   receiving reflected light from the determination target object emitted with the light;
   calculating an absorption spectrum of the determination target object based on the reflected light; and
   determining whether or not a brominated flame retardant is contained in the determination target object based on, in the absorption spectrum, an absorption spectrum in a wavelength band of 1.40 μm or more and 2.50 μm or less, wherein
   it is determined whether or not the brominated flame retardant is contained in the determination target object based on, in the absorption spectrum in the wavelength band of 1.40 μm or more and 2.50 μm or less, an absorption spectrum of at least one of wavelength bands including a wavelength band of 1.42 μm or more and 1.44 μm or less, a wavelength band of 1.45 μm or more and 1.47 μm or less, a wavelength band of 1.66 μm or more and 1.68 μm or less, a wavelength band of 1.72 μm or more and 1.74 μm or less, a wavelength band of 1.92 μm or more and 1.94 μm or less, a wavelength band of 2.11 μm or more and 2.12 μm or less, a wavelength band of 2.17 μm or more and 2.20 μm or less, and a wavelength band of 2.31 μm or more and 2.34 μm or less.

2. The brominated flame retardant determining method according to claim 1, wherein the determination target object is composed of ABS resin, and in determining whether or not the brominated flame retardant is contained in the determination target object, determining whether or not the brominated flame retardant is contained in the determination target object based on, in the absorption spectrum, the absorption spectrum of at least one of the wavelength band of 1.42 µm or more and 1.44 µm or less and the wavelength band of 1.45 µm or more and 1.47 µm or less.

3. The brominated flame retardant determining method according to claim 1, wherein
the brominated flame retardant is a bromine compound.

4. The brominated flame retardant determining method according to claim 1, wherein
the brominated flame retardant is one of PBB, PBDE, HBCDD, TBBPA, TBBPA-bis, and a TBBPA derivative.

5. The brominated flame retardant determining method according to claim 1, wherein
in the receiving the reflected light,
dispersing the reflected light from the determination target object emitted with the light, for each of the wavelength bands, and
the reflected light being dispersed is received for each of the wavelength bands.

6. A brominated flame retardant determining method, comprising:
emitting light to a determination target object composed of resin;
receiving reflected light from the determination target object emitted with the light;
calculating an absorption spectrum of the determination target object based on the reflected light; and
determining whether or not a brominated flame retardant is contained in the determination target object based on, in the absorption spectrum, an absorption spectrum in a wavelength band of 1.40 µm or more and 2.50 µm or less, wherein
in determining whether or not the brominated flame retardant is contained in the determination target object,
determining a type of the resin of the determination target object,
determining priorities of the wavelength bands based on a result of the determination of the type of the resin of the determination target object, and
determining whether or not the brominated flame retardant is contained in the determination target object based on an absorption spectrum in the wavelength in accordance with the priorities of the wavelength bands.

7. A recycling method, comprising:
conveying a plurality of determination target objects each composed of resin;
thereafter, applying the brominated flame retardant determining method according to claim 1 to the determination target objects which have conveyed; and
thereafter, selectively separating the determination target objects into a determination target object determined to contain a brominated flame retardant and a determination target object determined to be free of the brominated flame retardant, to thereby reuse the determination target object determined to be free of the brominated flame retardant.

8. A brominated flame retardant determining apparatus, comprising:
an emission unit that emits light to a determination target object composed of resin;
a light receiving unit that receives reflected light from the determination target object emitted with the light; and
an arithmetic processing unit that calculates an absorption spectrum of the determination target object based on the reflected light, wherein
the arithmetic processing unit determines whether or not a brominated flame retardant is contained in the determination target object based on, in the absorption spectrum, an absorption spectrum in a wavelength band of 1.40 µm or more and 2.50 µm or less, wherein
the arithmetic processing unit determines whether or not a brominated flame retardant is contained in the determination target object based on, in the absorption spectrum in the wavelength band of 1.40 µm or more and 2.50 µm or less, an absorption spectrum of at least one of wavelength bands including a wavelength band of 1.42 µm or more and 1.44 µm or less, a wavelength band of 1.45 µm or more and 1.47 µm or less, a wavelength band of 1.66 µm or more and 1.68 µm or less, a wavelength band of 1.72 µm or more and 1.74 µm or less, a wavelength band of 1.92 µm or more and 1.94 µm or less, a wavelength band of 2.11 µm or more and 2.12 µm or less, a wavelength band of 2.17 µm or more and 2.20 µm or less, and a wavelength band of 2.31 µm or more and 2.34 µm or less.

9. The brominated flame retardant determining apparatus according to claim 8, wherein
the determination target object is composed of ABS resin, and
the arithmetic processing unit determines whether or not the brominated flame retardant is contained in the determination target object based on, in the absorption spectrum, an absorption spectrum in at least one of the wavelength band of 1.42 µm or more and 1.44 µm or less and the wavelength band of 1.45 µm or more and 1.47 µm or less.

10. The brominated flame retardant determining apparatus according to claim 8, wherein
the brominated flame retardant is a bromine compound.

11. The brominated flame retardant determining apparatus according to claim 8, wherein
the brominated flame retardant is one of PBB, PBDE, HBCDD, TBBPA, TBBPA-bis, and a TBBPA derivative.

12. The brominated flame retardant determining apparatus according to claim 8, further comprising
a diffraction grating that disperses the reflected light from the determination target object emitted with the light for each of the wavelength bands, wherein
the light receiving unit receives the reflected light being dispersed by the diffraction grating, for each of the wavelength bands.

13. A brominated flame retardant determining apparatus, comprising:
an emission unit that emits light to a determination target object composed of resin;
a light receiving unit that receives reflected light from the determination target object emitted with the light; and
an arithmetic processing unit that calculates an absorption spectrum of the determination target object based on the reflected light, wherein
the arithmetic processing unit determines whether or not a brominated flame retardant is contained in the determination target object based on, in the absorption spectrum, an absorption spectrum in a wavelength band of 1.40 µm or more and 2.50 µm or less, wherein
the arithmetic processing unit comprises:

a resin determining unit that determines a type of the resin of the determination target object;

a priority determining unit that determines priorities of the wavelength bands based on a result of the determination of the resin determining unit; and a determining unit that determines whether or not the brominated flame retardant is contained in the determination target object based on an absorption spectrum in the wavelength band in accordance with the priorities of the wavelength bands determined by the priority determining unit.

14. A recycling apparatus, comprising:

a conveying unit that conveys a plurality of determination target objects each composed of resin;

the brominated flame retardant determining apparatus according to claim 8; and a selectively separating unit that selectively separates the determination target objects into a determination target object determined to be containing a brominated flame retardant and a determination target object determined to be free of the brominated flame retardant.

* * * * *